US011655302B2

(12) United States Patent
Chiron Blondel et al.

(10) Patent No.: US 11,655,302 B2
(45) Date of Patent: May 23, 2023

(54) ANTI-CD38 ANTIBODIES AND FORMULATIONS

(71) Applicant: SANOFI, Paris (FR)

(72) Inventors: Marielle Chiron Blondel, Paris (FR); Cendrine Lemoine, Paris (FR); Angela Virone-Oddos, Paris (FR); Béatrice Cameron, Paris (FR); Jacques Dumas, Paris (FR); Alain Fournier, Paris (FR); Jonathan Kingsbury, Bridgewater, NJ (US); Brian Murray, Bridgewater, NJ (US); Nathan Ostberg, Bridgewater, NJ (US); Sanket Patke, Bridgewater, NJ (US); Zichuan Zhang, Bridgewater, NJ (US)

(73) Assignee: SANOFI, Paris (FR)

( * ) Notice: Subject to any disclaimer, the term of this patent is extended or adjusted under 35 U.S.C. 154(b) by 395 days.

(21) Appl. No.: 16/896,784

(22) Filed: Jun. 9, 2020

(65) Prior Publication Data
US 2020/0399391 A1 Dec. 24, 2020

Related U.S. Application Data

(60) Provisional application No. 62/859,699, filed on Jun. 10, 2019.

(30) Foreign Application Priority Data

Feb. 17, 2020 (EP) .................................... 20305146

(51) Int. Cl.
C07K 16/28 (2006.01)
A61K 47/26 (2006.01)
A61K 9/19 (2006.01)
A61K 47/18 (2017.01)

(52) U.S. Cl.
CPC ............ C07K 16/2896 (2013.01); A61K 9/19 (2013.01); A61K 47/183 (2013.01); A61K 47/26 (2013.01); C07K 2317/72 (2013.01); C07K 2317/732 (2013.01); C07K 2317/92 (2013.01); C07K 2317/94 (2013.01)

(58) Field of Classification Search
CPC .......... C07K 16/2896; C07K 2317/732; C07K 2317/92; C07K 2317/94; A61K 9/19; A61K 47/183; A61K 47/26
See application file for complete search history.

(56) References Cited

U.S. PATENT DOCUMENTS

| | | | |
|---|---|---|---|
| 5,064,413 A | 11/1991 | McKinnon et al. | |
| 5,449,345 A | 9/1995 | Taylor et al. | |
| 5,954,695 A | 9/1999 | Sims et al. | |
| 6,428,509 B1 | 8/2002 | Fielder | |
| 6,645,177 B1 | 11/2003 | Shearn | |
| 7,195,610 B1 | 3/2007 | Flachbart | |
| 8,231,576 B2 | 7/2012 | Sims et al. | |
| 8,814,830 B2 | 8/2014 | Morris et al. | |
| 2016/0058863 A1 | 3/2016 | Johnston et al. | |
| 2021/0188996 A1 | 6/2021 | Huille et al. | |
| 2022/0218607 A1 | 7/2022 | Saluja et al. | |

FOREIGN PATENT DOCUMENTS

| | | | | |
|---|---|---|---|---|
| WO | WO 2006/023148 A2 | 3/2006 | | |
| WO | WO 2006/099875 A1 | 9/2006 | | |
| WO | WO 2008/047242 A2 | 4/2008 | | |
| WO | WO 2010/061357 A1 | 6/2010 | | |
| WO | WO 2010/061358 A1 | 6/2010 | | |
| WO | WO 2010/061359 A1 | 6/2010 | | |
| WO | WO 2010/061360 A1 | 6/2010 | | |
| WO | WO 2012/076663 A1 | 6/2012 | | |
| WO | WO-2013059885 A2 * | 5/2013 | ........... | A61K 47/642 |
| WO | WO 2014/074528 A2 | 5/2014 | | |
| WO | WO 2014/079886 A1 | 5/2014 | | |
| WO | WO 2014/089416 A1 | 6/2014 | | |
| WO | WO 2014/159911 A1 | 10/2014 | | |
| WO | WO 2015/066450 A1 | 5/2015 | | |
| WO | WO 2016/109822 A1 | 7/2016 | | |
| WO | WO 2017/079150 A1 | 5/2017 | | |
| WO | WO 2018/005881 A1 | 1/2018 | | |
| WO | WO 2018/119142 A1 | 6/2018 | | |
| WO | WO 2018/119299 A1 | 6/2018 | | |
| WO | WO 2020/160020 A1 | 8/2020 | | |
| WO | WO 2020/216847 A1 | 10/2020 | | |

OTHER PUBLICATIONS

Colombian Office Action No. 3725 regarding the Opposition filed by Laboratorios Legrand S.A. in parallel Columbian Patent Application No. NC2021/0015561, dated Mar. 22, 2022.
International Search Report and Written Opinion for PCT International Patent Application No. PCT/EP2020/061340, dated Jul. 28, 2020.
International Search Report and Written Opinion for PCT International Patent Application No. PCT/US2020/063452, dated Mar. 18, 2021.
Kumar et al., "International Myeloma Working Group consensus criteria for response and minimal residual disease assessment in multiple myeloma", Lancet Oncol., Aug. 2016, 17(8): e328-e346.
Oken et al., "Toxicity and response criteria of the Eastern Cooperative Oncology Group", Am. J. Clin. Oncol., Dec. 1982, 5(6): 649-655.
Shu et al., "Blockade of CD38 diminishes lipopolysaccharide-induced macrophage classical activation and acute kidney injury involving NF-kB signaling suppression", Cell Signal, Jan. 2018, 42: 249-258.

(Continued)

Primary Examiner — Jeffrey Stucker
Assistant Examiner — Laura Ann Essex
(74) Attorney, Agent, or Firm — Lathrop GPM LLP; James H. Velema, Esq.; Michael Spellberg

(57) ABSTRACT

Provided herein are antibodies that specifically bind human CD38, formulations and unit dosage forms comprising the antibodies, methods of preparing the antibodies and methods of using the antibodies.

24 Claims, 2 Drawing Sheets
Specification includes a Sequence Listing.

(56) References Cited

OTHER PUBLICATIONS

Arnulf et al., "Updated survival analysis of a randomized phase III study of subcutaneous versus intravenous bortezomib in patients with relapsed multiple myeloma", Haematologica, 2012, vol. 97, No. 12, pp. 1925-1928.
Baek et al., "Effects of Histidine and Sucrose on the Biophysical Properties of a Monoclonal Antibody", Pharmaceutical Research, Dec. 29, 2016, vol. 34, No. 3, pp. 629-639.
Daugherty et al., "Chapter 8: Formulation and delivery issues for monoclonal antibody therapeutics", Current Trends in Monoclonal Antibody Development and Manufacturing, Jan. 2010, pp. 103-129.
Derer et al., "Increasing FcγRIIa affinity of an FcγRIII-optimized anti-EGFR antibody restores neutrophil-mediated cytotoxicity", MAbs, Mar.-Apr. 2014, vol. 6, No. 2, pp. 409-421.
Dilillo et al., "Differential Fc-receptor engagement drives an antitumor vaccinal effect", Cell, May 21, 2015, vol. 161, No. 5, pp. 1035-1045.
Durie et al., "Bortezomib with lenalidomide and dexamethasone versus lenalidomide and dexamethasone alone in patients with newly diagnosed myeloma without intent for immediate autologous stem-cell transplant (SWOG S0777): a randomised, open-label, phase 3 trial", Lancet, Feb. 4, 2017, vol. 389, Issue 10068, pp. 519-527.
Empliciti® (elotuzumab) [package insert], U.S. Food and Drug Administration website, Obtained from: <www.accessdata.fda.gov/drugsatfda_docs/label/2018/761035s008lbl.pdf>, Revised Nov. 2018.
Gao et al., "Monoclonal antibody humanness score and its applications", BMC Biotechnology, Biomed Central Ltd., Jul. 5, 2013, vol. 13, No. 1, p. 55.
Graham et al., "Characteristics of a human cell line transformed by DNA from human adenovirus type 5", J. Gen Virol., Jul. 1977, vol. 36, No. 1, p. 59.
He et al., "Effect of Sugar Molecules on the Viscosity of High Concentration Monoclonal Antibody Solutions", Pharm Res., 2011, vol. 28, No. 7, pp. 1552-1560.
International Search Report and Written Opinion for PCT International Patent Application No. PCT/US2020/029531, dated Aug. 14, 2020, 15 pages.
Kumar et al., "Randomized, multicenter, phase 2 study (Evolution) of combinations of bortezomib, dexamethasone, cyclophosphamide, and lenalidomide in previously untreated multiple myeloma", Blood, 2012, vol. 119, No. 19, pp. 4375-4382.
Lazar et al., "Engineered antibody Fc variants with enhanced effector function", Proc. Natl. Acad. Sci. USA, Mar. 14, 2006, vol. 103, No. 11, pp. 4005-4010.
Lin et al., "Flow cytometric immunophenotypic analysis of 306 cases of multiple myeloma", Am J Clin Pathol., 2004, vol. 121, Issue 4, pp. 482-488.
Martin et al., "A phase 1b study of isatuximab plus lenalidomide and dexamethasone for relapsed/refractory multiple myeloma", Blood, 2017, vol. 129, No. 25, pp. 3294-3303.
Mather et al., "Culture of Testicular Cells in Hormone-Supplemented Serum-Free Medium", Annals of the NY Academy of Sciences, 1982, vol. 383, Issue 1, pp. 44-68.
Mather, "Establishment and characterization of two distinct mouse testicular epithelial cell lines", Biol. Reprod., 1980, vol. 23, No. 1, pp. 243-251.
Miltenyi Biotec, "CD14 MicroBeads human", Order No. 130-050-201, 2007, pp. 1-4.
Ocio et al., "Future agents and treatment directions in multiple myeloma", Expert RevHematol., 2014, vol. 7, No. 1, pp. 127-141.
Reinherz et al., "Discrete stages of human intrathymic differentiation: analysis of normal thymocytes and leukemic lymphoblasts of T-cell lineage", Proc Natl Acad Sci USA, Mar. 1980, vol. 77, No. 3, pp. 1588-1592.
Richards et al., "Optimization of antibody binding to FcgammaRIIa enhances macrophage phagocytosis of tumor cells", Mol Cancer Ther., Aug. 2008, vol. 7, No. 8, pp. 2517-2527.
Richardson et al., "A phase III randomized, open label, multicenter study comparing isatuximab, pomalidomide, and low-dose dexamethasone versus pomalidomide and low-dose dexamethasone in patients with relapsed/refractory multiple myeloma (RRMM)", Journal of Clinical Oncology, 2019, vol. 37, Issue 15, Supplement, Abstract 8004.
Richardson et al., "Lenalidomide, bortezomib, and dexamethasone combination therapy in patients with newly diagnosed multiple myeloma", Blood, Aug. 5, 2010, vol. 116, No. 5, pp. 679-686.
Roussel et al., "Front-line transplantation program with lenalidomide, bortezomib, and dexamethasone combination as induction and consolidation followed by lenalidomide maintenance in patients with multiple myeloma: a phase II study by the Intergroupe Francophone du Myélome", J Clin Oncol., Sep. 2014, vol. 32, No. 25, pp. 2712-2717.
Shire et al., "Challenges in the development of high protein concentration formulations", Journal of Pharmaceutical Sciences, American Chemical Society and American Pharmaceutical Association, Jun. 2004, vol. 93, No. 6, pp. 1390-1402.
Smith et al., "Mouse model recapitulating human Fcγ receptor structural and functional diversity", Proc Natl Acad Sci USA, 2012, vol. 109, No. 16, pp. 6181-6186.
Touzeau et al., "Daratumumab for the treatment of multiple myeloma", Expert Opinion on Biological Therapy, 2017, vol. 17, Issue 7, pp. 887-893.
Tzogani et al., "EMA Review of Panobinostat (Farydak) for the Treatment of Adult Patients with Relapsed and/or Refractory Multiple Myeloma", Oncologist, 2018, vol. 23, Issue 5, pp. 631-636.
Urlaub et al., "Isolation of Chinese hamster cell mutants deficient in dihydrofolate reductase activity", Proc. Natl. Acad. Sci. USA, 1980, vol. 77, No. 7, pp. 4216-4220.
Wang et al., "Antibody Structure Instability, and Formulation", Journal of Pharmaceutical Sciences, American Chemical Society and American Pharmaceutical Association, 2007, vol. 96, No. 1, pp. 1-26.
Wang et al., "IgG Fc engineering to modulate antibody effector functions", Protein & Cell, Oct. 6, 2017, vol. 9, No. 1, pp. 63-73.
Wang et al., "Viscosity-Lowering Effect of Amino Acids and Salts on Highly Concentrated Solutions of Two IgG1 Monoclonal Antibodies", Molecular Pharmaceutics, vol. 12, No. 12, pp. 4478-4487.
Yazaki et al., Methods in Molecular Biology, 2003, vol. 248, pp. 255-268.
U.S. Appl. No. 17/604,890 2022/0218607, filed Oct. 19, 2021 Jul. 14, 2022, Atul Saluja, Stable Low-Viscosity Antibody Formulations and Uses Thereof.
U.S. Appl. No. 16/896,784 2020/0399391, filed Jun. 9, 2020 Dec. 24, 2020, Marielle Chiron Blondel, Anti-CD38 Antibodies and Formulations.
U.S. Appl. No. 17/112,768 2021/0188996, filed Dec. 4, 2020 Jun. 24, 2021, Sylvain Huille, Formulations of Anti-CD38 Antibodies for Subcutaneous Administration.

* cited by examiner

ANTI-CD38 ANTIBODIES AND FORMULATIONS

RELATED APPLICATIONS

This application claims benefit of U.S. Provisional Application No. 62/859,699, filed Jun. 10, 2019, and European Patent Application No. 20305146.1, filed Feb. 17, 2020, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jun. 9, 2020, is named 704031_SA9-289_ST25.txt and is 44,667 bytes in size.

FIELD OF THE INVENTION

Provided herein are anti-CD38 antibodies having improved cytotoxic activity, and stable formulations thereof.

BACKGROUND OF THE INVENTION

CD38 is a Type II glycosylated 45 kilodalton (kDa) membrane protein that was identified as a lymphocyte marker. CD38 has a role in leukocyte homeostasis through modulation of hematopoietic cell survival and differentiation (Richards J O, et al., Mol Cancer Ther. 2008; 7(8): 2517-27). CD38 functions as a receptor binding to CD31 and is involved in cell adhesion and signal transduction. The function of CD38 in signal transduction appears to be versatile depending on the cell lineage, the differentiation stage, and, possibly, the association with different co-receptors (Richards J O, et al., 2008). CD38 is also an ectoenzyme catalyzing the synthesis and hydrolysis of cyclic adenosine-diphosphate-ribose (cADPR) from nicotinamide adenine dinucleotide (NAD+) to ADP-ribose (DiLillo D J, Ravetch J V., Cell. 2015; 161(5):1035-45). These reaction products are implicated in calcium mobilization and intracellular signaling (Derer S, et al., MAbs. 2014; 6(2):409-21).

The expression of CD38 in healthy humans can be detected on NK cells, monocytes, dendritic cells, macrophages, granulocytes, activated T and B cells, and plasma cells. In contrast, expression has not been detected in hematopoietic stem cells, resting T and B cells, or tissue macrophages. Furthermore, several hematological malignancies express CD38, such as plasma cell dyscrasias (e.g., multiple myeloma (MM), amyloidosis) and other cancers of hematopoietic origin including, including for example, Waldenstrom's disease, non-Hodgkin's lymphoma (NHL), acute lymphocytic leukemia (ALL), and acute myelogenous leukemia (AML).

The expression of CD38 is especially notable in MM as >98% of patients are positive for this protein (Reinherz E L, et al., Proc Natl Acad Sci USA. 1980; 77(3):1588-92, Lin P, et al., Am J Clin Pathol. 2004; 121(4):482-8). The strong and uniform expression of CD38 on malignant clonal MM cells contrasts with the restricted expression pattern on normal cells suggesting this antigen may be useful for specific targeting of tumor cells.

MM is a malignant plasma cell disease that is characterized by CD38 expression on the cell surface, clonal proliferation of plasma cells in the bone marrow (BM) and the production of excessive amounts of a monoclonal immunoglobulin (usually of the IgG or IgA type or free urinary light chain (also referred to as paraprotein, M-protein or M-component)). It is a disease predominantly associated with advancing age with more than 80% of patients aged 60 years or older.

The disease course for MM varies with the aggressiveness of the disease and related prognostic factors. Certain chromosomal abnormalities in multiple myeloma have been shown to be associated with poor clinical outcome. High-risk cytogenetic changes include del(17p), t(4;14), and t(14;16) and Iq gain, among others. During the two last decades, median survival has improved from 3 to 6 years; however, some patients can live longer than 10 years (Ocio E M, et al., Expert Rev Hematol. 2014; 7(1):127-41). Treatment options and survival are based on the patient's age, fitness and disease status. Patients under the age of approximately 65, presenting with symptomatic active disease in good physical health will generally receive initial therapy with autologous stem cell transplantation (ASCT). To achieve cytoreduction of the disease before collecting stem cells, induction chemotherapy is administered. Induction treatment regimens include alkylating agents, dexamethasone alone, thalidomide plus dexamethasone, and vincristine, Adriamycin® (doxorubicin), and dexamethasone (VAD; or modifications to this regimen); however, the latter two regimens are associated with higher toxicity (Richardson P G, et al., Blood. 2010; 116(5):679-86, Arnulf B, et al., Haematologica. 2012; 97:1925-8). Treatments with Velcade® (bortezomib) alone, bortezomib combinations, and Revlimid® (lenalidomide) plus dexamethasone have demonstrated improved outcomes as induction therapy, and these agents demonstrate higher response rates and lower toxicity (Richardson P G 2010, Kumar S, et al., Blood. 2012; 119(19): 4375-82; Roussel M, et al., J Clin Oncol. 2014; 32:2712-7; Durie B G M, et al., Lancet. 2017; 389:519-27). Additional approved drugs include pomalidomide (belonging to the same IMiD® class as lenalidomide) and carfilzomib and ixazomib (belonging to the same proteasome inhibitor class as bortezomib). In addition to these new treatments, monoclonal antibodies, particularly anti-CD38 antibodies, have begun to play a major role in the treatment of myeloma patients. Daratumumab, an anti-CD38 antibody, has been approved for treatment of MM as a single agent and in combination with other treatments for MM (Touzeau C, Moreau P., Expert Opin Biol Ther. 2017; 17(7):887-93; Tzogani K., et al., Oncologist. 2018; 23:1-11). Isatuximab, an anti-CD38 antibody, has been reported to induce 25-29% response rate as a single agent and 60% response rate in combination therapy in relapsed or refractory multiple myeloma (Martin T, et al., Blood. 2017; 129(25):3294-303); recent results of phase 3 study indicated that the addition of isatuximab is able to improve the progression-free survival with pomalidomide-dexamethasone in relapsed and refractory multiple myeloma (J Clin Oncol 37, 2019 (suppl; abstr 8004)). In addition, elotuzumab, an anti-Slam-F7 antibody, has been approved in combination with lenalidomide and dexamethasone for treatment of adult patients with MM who have received one to three prior lines of therapy, and in combination with pomalidomide and dexamethasone for the treatment of adult patients with MM who have received at least two prior therapies including lenalidomide and a proteasome inhibitor (Bristol-Myers Squibb Company. EMPLICITI® (elotuzumab) [package insert]. U.S. Food and Drug Administration website. www-dot-accessdata-dot-fda.gov/drugsatfda_docs/label/2018/761035s008lbl.pdf. Revised November 2018.

The current aim of therapy for these CD38-expressing diseases is to control the disease as effectively as possible, to maximize quality of life and to prolong survival. For example, MM patients will receive an average of 4 to 8 different regimens during their lifespan. Thus, despite the improvement in patient outcomes with newer therapies, MM a remains fatal disease. Thus, the treatment of patients who have received and progressed on current therapies, including antibody therapies, remains a significant challenging unmet medical need.

SUMMARY OF THE INVENTION

Compared to currently available treatments for CD38-expressing diseases, including antibody treatments, it is contemplated that the antibodies, uses, and methods of treatment provided herein may provide a superior clinical response or treatment of the disease. Provided herein are antibodies that specifically bind human CD38 and mediate superior killing of cells that express CD38, formulations and unit dosage forms comprising the antibodies, methods of preparing the antibodies, and methods of using the antibodies.

In one aspect, antibodies that specifically bind human CD38 are provided. In some embodiments, the antibodies provided herein comprise a light chain (LC) having an amino acid sequence selected from the group consisting of SEQ ID NOs: 7, 8, and 9 and a heavy chain (HC) having an amino acid sequence selected from the group consisting of SEQ ID NOs: 2, 3, 4, 5, and 6.

In some embodiments, the antibodies provided herein comprise an LC having an amino acid sequence of SEQ ID NO: 7 and an HC having an amino acid sequence selected from the group consisting of: SEQ ID NO: 2, SEQ ID NO: 3, and SEQ ID NO: 4. In some embodiments, the antibodies provided herein comprise an LC having an amino acid sequence of SEQ ID NO: 7 and an HC having an amino acid sequence of SEQ ID NO: 2. In some embodiments, the antibodies provided herein comprise an LC having an amino acid sequence of SEQ ID NO: 7 and an HC having an amino acid sequence of SEQ ID NO: 3. In some embodiments, the antibodies provided herein comprise an LC having an amino acid sequence of SEQ ID NO: 7 and an HC having an amino acid sequence of SEQ ID NO: 4.

In some embodiments, the antibodies provided herein comprise an LC having an amino acid sequence of SEQ ID NO: 8 and an HC having an amino acid sequence selected from the group consisting of SEQ ID NO: 5 and SEQ ID NO: 6. In some embodiments, the antibodies provided herein comprise and LC having an amino acid sequence of SEQ ID NO: 8 and HC having an amino acid sequence of SEQ ID NO: 5. In some embodiments, the antibodies provided herein comprise and LC having an amino acid sequence of SEQ ID NO: 8 and HC having an amino acid sequence of SEQ ID NO: 6.

In some embodiments, the antibodies provided herein comprise an LC having an amino acid sequence of SEQ ID NO: 9 and an HC having an amino acid sequence selected from the group consisting of SEQ ID NO: 6 and SEQ ID NO: 7. In some embodiments, the antibodies provided herein comprise and LC having an amino acid sequence of SEQ ID NO: 9 and HC having an amino acid sequence of SEQ ID NO: 6. In some embodiments, the antibodies provided herein comprise and LC having an amino acid sequence of SEQ ID NO: 9 and HC having an amino acid sequence of SEQ ID NO: 7.

In another aspect, pharmaceutical compositions comprising a formulated antibody are provided herein. In some embodiments of the pharmaceutical compositions, the antibody comprises HCs and LCs having the amino acid sequences as described above, in combination with sucrose, L-histidine, and polysorbate 80. In some embodiments, the antibody is present at a concentration of 50 mg/mL, the sucrose is present at a concentration of 8% (w/v), the L-histidine is present at a concentration of 10 mM, the polysorbate 80 (PS80) is present at a concentration of 0.05% (v/v), and the formulation has a pH of 6.2. In some embodiments, the pharmaceutical composition is lyophilized.

In another aspect, unit dosage forms comprising a formulated antibody are provided herein. In some embodiments, the antibody comprises HCs and LCs having the amino acid sequences as described above and the unit dosage form comprises 215 mg of the antibody, 6.21 mg L-histidine, 344 mg sucrose, and 2.15 mg polysorbate 80. In some embodiments, the unit dosage form of the antibody is lyophilized.

In another aspect, processes for preparing pharmaceutical compositions comprising an antibody that specifically binds human CD38 are provided herein. In some embodiments, the antibody comprises HCs and LCs having the amino acid sequences as described above, wherein the process comprises expressing the antibody in a cell culture, subjecting the antibody to at least one of a chromatography purification step and an ultrafiltration step to produce a purified antibody solution; and adjusting the purified antibody solution to produce an antibody formulation. In some embodiments, the antibody formulation comprises the purified antibody, sucrose, L-histidine, and polysorbate 80. In some embodiments, antibody formulation comprises the antibody at a concentration of 50 mg/mL, sucrose at a concentration of 8% w/v, L-histidine at a concentration of 10 mM; and polysorbate 80 (PS80) at a concentration of 0.05% v/v. In some embodiments, the antibody formulation is prepared such that it has a pH of 6.2. In some embodiments of the process for preparing the antibody formulation, the antibody formulation is lyophilized.

In another aspect, methods for preparing a reconstituted antibody formulation are provided. In some embodiments, the lyophilized antibody formulation comprises sucrose, L-histidine, PS80, and an antibody that specifically binds human CD38. In some embodiments, the antibody comprises HCs and LCs having the amino acid sequences as described above. In some embodiments, the lyophilized antibody formulation is reconstituted in a diluent, thereby preparing the reconstituted antibody formulation. In some embodiments, the reconstituted antibody formulation comprises the antibody at a concentration of 50 mg/mL, sucrose at a concentration of 8% w/v, L-histidine at a concentration of 10 mM; and PS80 at a concentration of 0.05% v/v. In some embodiments, the reconstituted antibody formulation has a pH of 6.2.

In another aspect, methods of treating a patient having a Multiple Myeloma are provided. In some embodiments, the method comprises administering to the patient one or more doses of an antibody that specifically binds human CD38, wherein the antibody comprises HCs and LCs having the amino acid sequences as described above.

In another aspect, antibodies for use in a method of treating Multiple Myeloma are provided. In some embodiments, the antibody specifically binds human CD38, wherein the antibody comprises HCs and LCs having the amino acid sequences as described above.

DETAILED DESCRIPTION OF THE INVENTION

Figure 1:
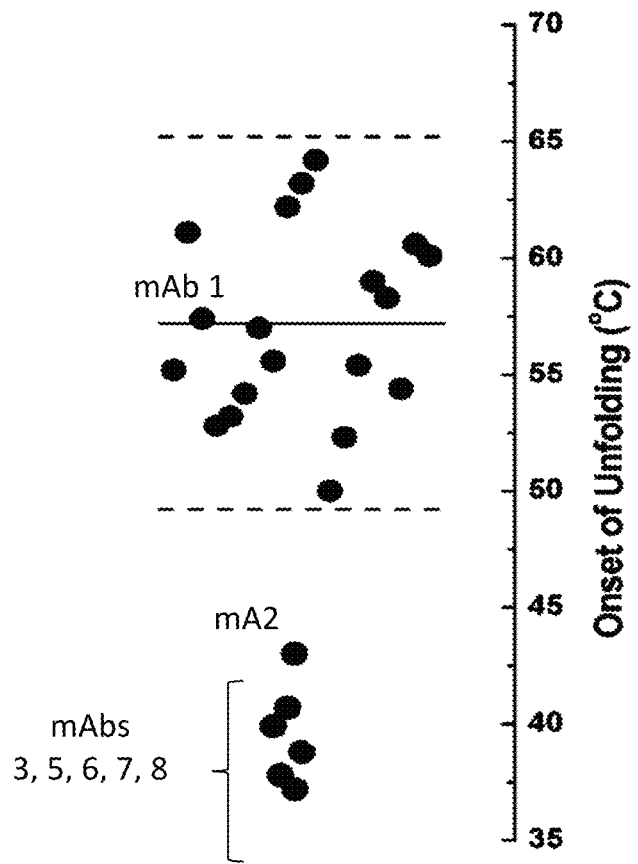
FIG. 1 is a graph showing the onset of unfolding for mAbs 1, 2, 3, 5, 6, 7, and 8.
Figure 2:
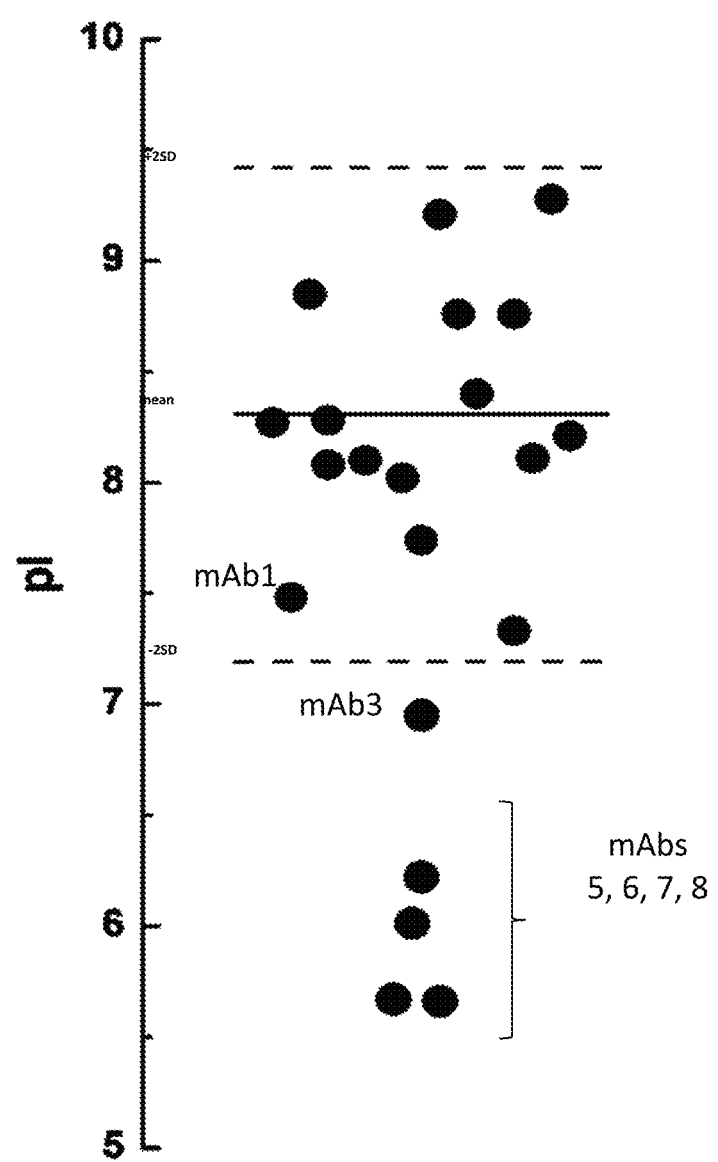
FIG. 2 is a graph showing isoelectric point (pI) for mAbs 1, 3, 5, 6, 7, and 8.

Provided herein are anti-CD38 antibodies that have superior antibody-dependent cellular cytotoxicity (ADCC) against cells expressing high, medium, and low levels of CD38 on their cell surfaces. In some embodiments, the anti-CD38 antibodies provided herein also have superior antibody-dependent cellular phagocytosis (ADCP) activity against cells expressing CD38 on their cell surfaces. In some embodiments, the antibodies provided herein have a lower than expected isoelectric point (pI). Despite the lower than expected pI and onset of protein unfolding at a lower temperature, which could negatively impact the stability of the antibody, especially in commercial production processes, the antibodies provided herein are provided in stable suitable form for administration to human patients.

Antibodies

Provided herein are anti-CD38 antibodies that specifically bind human CD38. The anti-CD38 antibodies provided herein may be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. The vector is typically transformed into a host cell suitable for expression of the nucleic acid. In some embodiments, the host cell is a eukaryotic cell or a prokaryotic cell. In some embodiments, the eukaryotic host cell is a mammalian cell. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J., 2003), pp. 255-268. The anti-CD38 antibody prepared from the cells can be purified using, for example, hydroxylapatite chromatography, hydrophobic interaction chromatography, gel electrophoresis, dialysis, and affinity chromatography, with affinity chromatography being among one of the typically preferred purification steps. In general, various methodologies for preparing antibodies for use in research, testing, and clinical applications are well-established in the art, consistent with the above-described methodologies and/or as deemed appropriate by one skilled in the art.

In some embodiments, the antibody is expressed by the CHO 8D6 host cell line (DXB11 derivative) using a 500 L single-use bioreactor, operated in fed-batch mode. The cell culture process is initiated by thawing a master cell bank vial, followed by a series of seed train cell expansion steps. The cells are then transferred into a bioreactor and grown using a serum free, chemically-defined cell culture medium. The culture is terminated for harvest of the antibodies after 10-14 days. The cells and cell culture debris can be removed from the harvested cell culture by depth filtration.

Harvested material is then further processed through chromatographic and filtration steps to produce purified antibody. The purified antibody is formulated in a liquid solution and is stored at ≤−30° C.

Prior to dispensing the formulated antibody into suitable vials, the liquid solution is thawed and sterile filtered using a 0.2 µm filtration device. The formulated antibody is dispensed into a suitable container, such as a USP Type 1 glass vial, 4.3 mL/vial. In some embodiments, the filled vial includes a 0.3 mL overage of the formulated antibody. In some embodiments, the formulated antibody is lyophilized in the vial.

The term "antibody" typically refers to a tetrameric protein comprising two heavy chains (HC) and two light chains (LC). Each such tetramer is typically composed of two identical pairs of polypeptide chains, each pair having one LC (typically having a molecular weight of about 25 kDa) and one HC (typically having a molecular weight of about 50-70 kDa). The terms "HC" and "LC" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a typical antibody, a full-length HC immunoglobulin polypeptide includes a variable domain (VH) and three constant domains (CH1, CH2, and CH3), wherein the VH domain is at the amino-terminus of the polypeptide and the CH3 domain is at the carboxyl-terminus, and a full-length LC immunoglobulin polypeptide includes a variable domain (VL) and a constant domain (CL), wherein the VL domain is at the amino-terminus of the polypeptide and the CL domain is at the carboxyl-terminus.

The term "antibody" is used herein in the broadest sense and specifically covers typical antibodies, as described above, including monoclonal antibodies, and multispecific antibodies (e.g., bi and tri-specific antibodies so long as they exhibit the desired biological activity including specific binding to the CD38 target and ability to trigger ADCC and ADCP).

The term "Fc" as used herein refers to a molecule comprising the sequence of a non-antigen-binding fragment resulting from digestion of an antibody or produced by other means, whether in monomeric or multimeric form, and can contain the hinge region. Fc molecules are made up of monomeric polypeptides that can be linked into dimeric or multimeric forms by covalent (i.e., disulfide bonds) and non-covalent association. The number of intermolecular disulfide bonds between monomeric subunits of typical Fc molecules ranges from 1 to 4 depending on class (e.g., IgG, IgA, and IgE) or subclass (e.g., IgG1, IgG2, IgG3, IgA1, IgGA2, and IgG4). One example of a Fc is a disulfide-bonded dimer resulting from papain digestion of an IgG.

The antibodies described herein may be isolated. The term "isolated protein", "isolated polypeptide" or "isolated antibody" refers to a protein, polypeptide or antibody that by virtue of its origin or source of derivation (1) is not associated with naturally associated components that accompany it in its native state, (2) is substantially free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

In some embodiments, the antibodies provided herein comprise HC and LC amino acid sequences as provided in Table 1.

TABLE 1

| mAb | HC SEQ ID NO: | LC SEQ ID NO: |
|---|---|---|
| 2 | 2 | 7 |
| 3 | 3 | 7 |
| 4 | 4 | 7 |
| 5 | 5 | 8 |
| 6 | 5 | 9 |
| 7 | 6 | 8 |
| 8 | 6 | 9 |
| 9 | 10 | 7 |

Binding Properties

The term "affinity" refers to a measure of the attraction between two polypeptides, such as receptor/ligand or antigen/antibody, for example. The intrinsic attractiveness between two polypeptides can be expressed as the binding affinity equilibrium constant (KD) of a particular interaction. An antibody is said to specifically bind to an antigen when the KD is ≤1 µM, preferably ≤100 nM. A KD binding affinity constant can be measured, e.g., by surface plasmon resonance (SPR) (BIAcore®) or Bio-Layer Interferometry.

The term "koff" refers to the dissociation rate constant of a particular antibody-antigen interaction. A koff dissociation rate constant can be measured, e.g., by Bio-Layer Interferometry.

Binding to CD38

In some embodiments, the antibodies provided herein comprise a tetrameric protein comprising two HCs and two LCs and binds to human CD38 with an affinity or KD of about $1.91 \times 10^{-10}$ M to about $6.7 \times 10^{-10}$ M when measured by Surface Plasmon Resonance (SPR) as described below. In some embodiments, the HC and LC have the amino acid sequences of SEQ ID NOs: 2 and 7 (mAb 2), 3 and 7 (mAb 3), 4 and 7 (mAb 4), 5 and 8 (mAb 5), 5 and 9 (mAb 6), 6 and 8 (mAb 7), or 6 and 9 (mAb 8), respectively.

In some embodiments, the antibody comprises HC and LC having the amino acid sequences of SEQ ID NOs: 3 and 7, respectively, and the antibody binds to human CD38 with an affinity or KD of about $2 \times 10^{-10}$ M. In some embodiments, the antibody comprises HC and LC having the amino acid sequences of SEQ ID NOs: 5 and 8, respectively, and the antibody binds to human CD38 with an affinity or KD of about $6.7 \times 10^{-10}$ M. In some embodiments, the antibody comprises HC and LC having the amino acid sequences of SEQ ID NOs: 5 and 9, respectively, and the antibody binds to human CD38 with an affinity or KD of about $4.15 \times 10^{-10}$ M. In some embodiments, the antibody comprises HC and LC having the amino acid sequences of SEQ ID NOs: 6 and 8, respectively, and the antibody binds to human CD38 with an affinity or KD of about $3.85 \times 10^{-10}$ M. In some embodiments, the antibody comprises HC and LC having the amino acid sequences of SEQ ID NOs: 6 and 9, respectively, and the antibody binds to human CD38 with an affinity or KD of about $1.91 \times 10^{-10}$ M.

Binding to FcγRIIIa (CD16a) and FcγRIIa (CD32a)

The antibodies provided herein are also capable of binding to the lower affinity FcγRIIIa (CD16a) variant having phenylalanine (F) at amino acid position 158 (158F) and are capable of binding to the higher affinity FcγRIIIa (CD16a) variant having valine (V) at amino acid position 158 (158V) with KDs within less than an order of magnitude, respectively, and with KDs of less than 100 nM as measured by SPR. In some embodiments, the antibodies provided herein bind to the 158F variant and to the 158V variant of FcγRIIIa (CD16a) with KDs of less than 100 nM as measured by SPR and where in the binding to the 158F and 158V variants differ by less than 2-fold. In some embodiments, the antibodies provided herein bind to FcγRIIIa (CD16a) variant (158F) with a KD of about 59 nM or less when measured, for example, by SPR.

In some embodiments, the antibody comprises an HC having an amino acid sequence of SEQ ID NO: 2 and an LC having an amino acid sequence of SEQ ID NO: 7 and is capable of binding to FcγRIIIa (158F) with a KD of about 53 nM and of binding to FcγRIIIa (158V) with a KD or about 47 nM as measured, for example, by SPR. In some embodiments, the antibody comprises an HC having an amino acid sequence of SEQ ID NO: 3 and an LC having an amino acid sequence of SEQ ID NO: 7 and is capable of binding to FcγRIIIa (158F) with a KD of about 59 nM and is capable of binding to FcγRIIIa (158V) with a KD of about 75 nM as measured, for example, by SPR. In some embodiments, the antibody comprises an HC having an amino acid sequence of SEQ ID NO: 4 and an LC having an amino acid sequence of SEQ ID NO: 7 and is capable of binding to FcγRIIIa (158F) with a KD of about 51 nM and is capable of binding to FcγRIIIa (158V) with a KD of about 47 nM as measured, for example, by SPR.

The antibodies provided herein are also capable of binding to the lower affinity FcγRIIa (CD32a) variant having arginine at amino acid position 131 (131R) with a KD of ≤690 nM and are capable of binding to the higher affinity FcγRIIa (CD32a) variant having a histidine at position 131 (131H) with a KD of less than about 270 nM as measured, for example, by SPR.

In some embodiments, the antibody comprises an HC having an amino acid sequence of SEQ ID NO: 2 and an LC having an amino acid sequence of SEQ ID NO: 7 and is capable of binding to FcγRIIa (CD32a) (131R) with a KD of about 690 nM and of binding to FcγRIIa (CD32a) (131H) with a KD or about 120 nM as measured, for example, by SPR. n some embodiments, the antibody comprises an HC having an amino acid sequence of SEQ ID NO: 3 and an LC having an amino acid sequence of SEQ ID NO: 7 and is capable of binding to FcγRIIa (CD32a) (131R) with a KD of ≤about 125 nM or ≤100 nM and is capable of binding to FcγRIIa (CD32a) (131H) with a KD of about 220 nm as measured, for example, by SPR. In some embodiments, the antibody comprises an HC having an amino acid sequence of SEQ ID NO: 4 and an LC having an amino acid sequence of SEQ ID NO: 7 and is capable of binding to FcγRIIa (CD32a) (131R) with a KD of about 510 nM and is capable of binding to FcγRIIa (CD32a) (131H) with a KD of about 60 nM as measured, for example, by SPR.

In some embodiments, the antibody is also capable of binding to FcγRIIIa (CD16a) 158F with apparent KD of about 70 nM or less and to FcγRIIIa (CD16a) 158V with apparent KD of about 32 nM or less as measured by binding to FcγRIIIa (CD16a) 158F- or 158V-expressing HEK cells, respectively. In some embodiments, the antibody comprising an HC having an amino acid sequence of SEQ ID NO: 2 and an LC having an amino acid sequence of SEQ ID NO: 7 is also capable of binding to FcγRIIIa (CD16a) 158F with apparent KD of about 70 nM and is capable of binding FcγRIIIa (CD16a) 158V with apparent KD of about 18 nM as measured by binding to FcγRIIIa (CD16a) 158F- or 158V-expressing HEK cells, respectively. In some embodiments, the antibody comprising an HC having an amino acid sequence of SEQ ID NO: 3 and an LC having an amino acid sequence of SEQ ID NO: 7 is also capable of binding to FcγRIIIa (CD16a) 158F with apparent KD of about 60 nM and is capable of binding FcγRIIIa (CD16a) 158V with apparent KD of about 32 nM as measured by binding to FcγRIIIa (CD16a) 158F- or 158V-expressing HEK cells, respectively. In some embodiments, the antibody comprising an HC having an amino acid sequence of SEQ ID NO: 4 and an LC having an amino acid sequence of SEQ ID NO: 7 is also capable of binding to FcγRIIIa (CD16a) 158F with apparent KD of about 44 nM and is capable of binding FcγRIIIa (CD16a) 158V with apparent KD of about 28 nM as measured by binding to FcγRIIIa (CD16a) 158F- or 158V-expressing HEK cells, respectively.

In some embodiments, the antibody is also capable of binding to FcγRIIa (CD32a) variant having arginine at amino acid position 131 (131R) with apparent KD of about 890 nM or less and to FcγRIIa (CD32a) variant 131H with apparent KD of about 840 nM or less as measured by binding to FcγRIIa (CD32a) 131R- or 131H-expressing HEK cells, respectively. In some embodiments, the antibody comprising an HC having an amino acid sequence of SEQ ID NO: 2 and an LC having an amino acid sequence of SEQ ID NO: 7 is also capable of binding to FcγRIIa (CD32a) 131R with apparent KD of about 890 nM and is capable of binding FcγRIIa (CD32a) 131H with apparent KD of about 840 nM as measured by binding to FcγRIIa (CD32a) 131R- or 131H-expressing HEK cells, respectively. In some embodiments, the antibody comprising an HC having an amino acid sequence of SEQ ID NO: 3 and an LC having an amino acid sequence of SEQ ID NO: 7 is also capable of binding to FcγRIIa (CD32a) 131R with apparent KD of about 87 nM and is capable of binding FcγRIIa (CD32a) 131H with apparent KD of about 222 nM as measured by binding to FcγRIIa (CD32a) 131R- or 131H-expressing HEK cells, respectively. In some embodiments, the antibody comprising an HC having an amino acid sequence of SEQ ID NO: 4 and an LC having an amino acid sequence of SEQ ID NO: 7 is also capable of binding to FcγRIIa (CD32a) 131R with apparent KD of about 467 nM and is capable of binding FcγRIIa (CD32a) 131H with apparent KD of about 544 nM as measured by binding to FcγRIIa (CD32a) 131R- or 131H-expressing HEK cells, respectively.

Mechanism of Action

The antibodies provided herein are capable of killing a CD38-expressing cell by Antibody Dependent Cellular Cytotoxicity (ADCC) of cells expressing high (~400,000/cell), medium (~100,000/cell), and low (~13,000/cell) levels of CD38 molecules on the cell surface. The antibodies provided herein trigger such ADCC in the presence of Natural Killer (NK) cells that express the lower affinity FcγIIIa (CD16a) receptor variant (158F) and/or express the higher affinity FcγIIIa (CD16a) receptor variant (158V). ADCC can be measured using methods known in the art, for example by measuring target cell lysis in the presence of the antibody and effector cells in a cell-based potency assay. The target cell can be, for example, a CD38 expressing cell such as KMS12-BM, RPMI-8226, or MOLP-8. In addition, the effector cells can be, for example, any cell that can be induced to kill target cells by ADCC. In some embodiments the effector cells are primary cells isolated from human blood such as peripheral blood mononuclear cells (PBMC) or human NK cells purified from PBMC. In another embodiment, the cells are a Natural Killer cell line such as NK-92 cells that express FcγRIIIa (158V) or FcγRIIIa (158F) on the surface of the cells (see WO 06/023148). In still other embodiments, the NK cell line is a cell line such as a Jurkat cell line that has been engineered to express FcγIIIa (CD16a) 158F or 158V (see for example Promega, G701A).

The antibodies provided herein are capable of killing cells expressing a high level of CD38 on the cell surface by Antibody Dependent Cellular Phagocytosis (ADCP). The antibodies provided herein trigger such ADCP in the presence of human PBMC. In one embodiment, the antibodies provided herein trigger about 41% phagocytosis of CD38-expressing cells by human PMBCs that express FcγRIIIa (158V) with a relative EC50 of 212.6 pM.

Pharmaceutical Compositions and Formulated Antibodies

The term "pharmaceutical formulation" refers to a preparation which is in such form as to permit the biological activity of the active ingredient to be effective, and which contains no additional components which are unacceptably toxic to a subject to which the formulation would be administered. Such formulations typically are sterile. "Pharmaceutically acceptable" excipients (vehicles, additives) are those which can reasonably be administered to a subject mammal to provide an effective dose of the active ingredient employed.

Pharmaceutical compositions and formulations of the antibodies provided herein can be prepared by mixing the antibody, having the desired degree of purity, with one or more optional pharmaceutically acceptable carriers (Remington's Pharmaceutical Sciences 16th edition, Osol, A. Ed. (1980)), and can be provided in the form of lyophilized formulations or aqueous solutions.

In some embodiments, the pharmaceutical compositions provided herein comprise a formulated antibody comprising an antibody and one or more of the following excipients: sucrose, L-histidine, and polysorbate 80 (PS80). In some embodiments, the antibodies comprise HC and LC amino acid sequences of any one of the monoclonal antibodies provided in Table 1. In some embodiments, the antibody is present in the pharmaceutical composition at a concentration of 5 mg/mL to 50 mg/mL. In some embodiments, the antibody is present in the pharmaceutical composition at a concentration of 5 mg/mL. In some embodiments, the antibody is present in the pharmaceutical composition at a concentration of 10 mg/mL. In some embodiments, the antibody is present in the pharmaceutical composition at a concentration of 20 mg/mL. In some embodiments, the antibody is present in the pharmaceutical composition at a concentration of 50 mg/mL. The concentration of each excipient is chosen such that the pharmaceutical composition can be diluted for administration by infusion. For example, in some embodiments, the sucrose is present at a concentration of 8% (w/v) to 10% (w/v). In some embodiments, the sucrose is present at a concentration of 8% (w/v). In other embodiments, the sucrose is present at a concentration of 10% (w/v). In some embodiments, the L-histidine is present at a concentration of 10 mM to 20 mM. In some embodiments, the L-histidine is present at a concentration of 10 mM. In some embodiments, the L-histidine is present at a concentration of 20 mM. In some embodiments, the PS80 is present at a concentration of 0.005% (v/v) to 0.05% (v/v). In some embodiments, the PS80 is present at a concentration of 0.005% (v/v). In some embodiments, the PS80 is present at a concentration of 0.02% (v/v). In some embodiments, the PS80 is present at a concentration of 0.05% (v/v). In some embodiments, the pH of the pharmaceutical composition is optimized to maintain stability of the antibody for example when the pharmaceutical composition is in liquid form. In some embodiments, the pH of the formulated antibody has a pH of about 6.0 to about 6.5. In some embodiments, the formulated antibody has a pH of about 6.0. In some embodiments, the formulated antibody has a pH of about 6.2. In some embodiments, the formulated antibody has a pH of about 6.5. In some embodiments, the formulated antibody has a pH of 6.0. In some embodiments, the formulated antibody has a pH of 6.2. In some embodiments, the formulated antibody has a pH of 6.5.

In some embodiments, the antibody of the pharmaceutical composition and/or formulated antibodies provided herein comprise one or more charged isoforms. Charged isoforms are typically described as main isoform, acidic isoform(s), and basic isoform(s). The main isoform refers to the most prevalent isoform in a given batch of antibody. Acidic isoform(s) have lower isoelectric point (pI) compared to the main isoform, and basic isoforms have higher pH compared to the main isoform. Charged isoforms can result from post-translational modifications to the amino acid sequence of the HC and/or LC. For example, increases in deamidation, glycation and sialylation, may cause a decrease in the pI of an antibody. Conversion of an N-terminal glutamic acid to pyroGlu (or pyroQ) results in the loss of one positive charge, which may cause a decrease in the pI. In addition, the presence of a C-terminal lysine may cause an increase the pI of an antibody. Furthermore, amidation of a C-terminal proline may cause an increase in pI of the antibody.

In some embodiments of the antibodies (including antibodies in the pharmaceutical composition, and formulated antibodies) provided herein, the amino acid at position 1 of the HC amino acid sequence is pyroglutamine. In some embodiments of the antibodies provided herein, the HC has a C-terminal amino acid consisting of glycine.

Charged isoforms of the antibodies provided herein can be separated and quantified using methods known in the art for separating polypeptides based on charge. For example, in some embodiments, a weak cation exchange column can be used in a high performance liquid chromatography (HPLC) system with a phosphate/sodium chloride gradient buffer. In this system, following loading of the antibody onto the column, the acidic isoforms of the antibody would elute first, followed by the main isoform and then the basic isoforms of the antibody. In another embodiment, capillary isoelectric focusing (cIEF) can be used. Capillary isoelectric focusing is a method that separates proteins by their isoelectric point (pI) values. In cIEF, the antibody sample migrates to its isoelectric points on a pH gradient within the capillary, thereby resolving the different charge isoforms along the length of the capillary. To identify and characterize the cIEF variants, charge isoforms can be isolated by strong cation exchange chromatography (SCX) and analyzed by cIEF. An image of the resolved charged isoforms in the capillary is taken using a charge coupled device camera using whole column detection and measuring absorbance at 280 nm. The charge isoform distribution of the test sample is compared to a reference standard using cIEF to identify the charge isoforms of the antibody. In some embodiments, cIEF is used as a quality control measure to confirm the identity of the antibody during commercial production, and by determining the charge isoform distribution of the antibody in comparison to a reference standard, e.g., a test antibody having a charge isoform distribution pattern within a pre-defined distribution pattern or compared to the distribution pattern of a reference standard.

In some embodiments, the antibodies (including antibodies in the pharmaceutical composition, and formulated antibodies) comprise HC and LC amino acid sequences of any one of the monoclonal antibodies provided in Table 1, and one or more charged isoform parameters selected from the group consisting of: at least about 70% main isoform, no more than about 30% acidic isoform, and less than 4% basic isoform. In some embodiments, the antibody comprises 71% main isoform, 28% acidic isoform, and less than 4% basic isoform. In some embodiments the antibody contains charge isoforms with isoelectric points ranging from about 5.8 to about 9.0. In some embodiments the antibody contains charge isoforms with isoelectric points ranging from about 5.85 to about 8.97.

In some embodiments, the antibodies (including antibodies in the pharmaceutical composition, and formulated antibodies) are lyophilized. The antibodies (including antibodies in the pharmaceutical composition, and formulated antibodies) can be in a container (e.g., a vial) such that a prescribed dose of the antibody can be removed from the container for administration to a patient.

Unit dosage forms of formulated antibodies that specifically bind CD38 are provided herein. In some embodiments, the antibodies comprise HC and LC amino acid sequences of any one of the monoclonal antibodies provided in Table 1, and the unit dosage form comprises the antibody and one or more excipients selected from the group of sucrose, L-histidine, and polysorbate 80. In some embodiments, the unit dosage form comprises about 215 mg of the antibody, about 6.21 mg L-histidine, about 344 mg sucrose, and about 2.15 mg polysorbate 80. In some embodiments, the unit dosage form comprises 215 mg of the antibody, 6.21 mg L-histidine, 344 mg sucrose, and 2.15 mg polysorbate 80. In some embodiments, the unit dosage form is lyophilized. The unit dosage form can be in a container (e.g., a vial) such that a prescribed dosage of the antibody can be removed from the container for administration to a patient. In some embodiments, the antibody, pharmaceutical formulation, and/or formulated antibody are in a glass vial fitted with elastomeric closure. In some embodiments, the vial contains about 215 mg of antibody. In some embodiments, the vial contains 215 mg of antibody. In some embodiments, the fill volume of the vial has been established to enable removal of about 4 mL. In some embodiments, the fill volume of the vial has been established to enable removal of 4 mL.

Process for Preparing

Provided herein are processes for preparing the antibody, pharmaceutical composition, and unit dosage forms. In some embodiments, the antibodies comprise HC and LC amino acid sequences of any one of the monoclonal antibodies provided in Table 1. In one embodiment, the process comprises expressing the antibody in a suitable cell culture. The antibody is subjected to at least one of a chromatography step and at least one ultrafiltration step, thereby producing a purified antibody solution. The purified antibody solution is adjusted to concentrate the antibody and to add excipients and adjust pH. In one embodiment, the concentration of the antibody is adjusted to be about 50 mg/ml; sucrose, L-histidine, and polysorbate 80 are added, and the pH is adjusted to be at least about 6.0. In one embodiment, the concentration of the antibody is adjusted to be 50 mg/ml; sucrose, L-histidine, and polysorbate 80 are added, and the pH is adjusted to be at least 6.0. In some embodiments, the pH is about 6.2. In some embodiments, the pH is 6.2. In some embodiments, the sucrose is at a concentration of about 8% w/v, the L-histidine is at a concentration of about 10 mM; and the polysorbate 80 is at a concentration of about 0.05% v/v. In some embodiments, the sucrose is at a concentration of 8% w/v, the L-histidine is at a concentration of 10 mM; and the polysorbate 80 is at a concentration of 0.05% v/v. In some embodiments, the antibody, pharmaceutical composition and/or formulated antibody are lyophilized.

In some embodiments methods of preparing reconstituted formulated antibody are provided wherein the formulated antibody is provided in lyophilized form and comprises HC and LC amino acid sequences of any one of the monoclonal antibodies provided in Table 1, sucrose at a concentration of about 8% w/v, L-histidine at a concentration of about 10 mM, and polysorbate 80 at a concentration of about 0.05% v/v. In some embodiments methods of preparing reconstituted formulated antibody are provided wherein the formulated antibody is provided in lyophilized form and comprises HC and LC amino acid sequences of any one of the monoclonal antibodies provided in Table 1, sucrose at a concentration of 8% w/v, L-histidine at a concentration of 10 mM, and polysorbate 80 at a concentration of 0.05% v/v. In some embodiments, prior to use the formulated antibody is reconstituted in a suitable volume of water for injection to produce a solution comprising the antibody at a concentration of about 50 mg/mL, sucrose at a concentration of about 8% w/v, L-Histidine at a concentration of about 10 mM, and polysorbate 80 at a concentration of about 0.05% v/v, wherein the pH of the reconstituted antibody is about 6.2. In some embodiments, prior to use the formulated antibody is reconstituted in a suitable volume of water for injection to produce a solution comprising the antibody at a concentration of 50 mg/mL, sucrose at a concentration of 8% w/v, L-Histidine at a concentration of 10 mM, and polysorbate 80 at a concentration of 0.05% v/v, wherein the pH of the reconstituted antibody is 6.2.

As used herein, the term "treatment" or "treating" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but not limited to, reducing the proliferation of cancerous cells, destroying cancerous cells, decreasing symptoms resulting from the disease, increasing the quality of life of those suffering from the disease, decreasing the dose of other medications required to treat the disease, and/or prolonging survival of individuals.

Provided herein are methods for treating or delaying progression of multiple myeloma (such as relapsed multiple myeloma or relapsed and refractory multiple myeloma) in an individual, comprising administering to a subject in need thereof an effective amount of an anti-CD38 antibody provided herein. In some embodiments, the antibodies comprise HC and LC amino acid sequences of any one of the monoclonal antibodies provided in Table 1. In some embodiments, the antibody is capable of improving survival of mice in a murine MM model, wherein mice in the model express the low affinity variant of human CD16a (158F), and wherein the mice have been injected with 500,000 EL4 cells expressing human CD38. In some embodiments, one or more doses of an anti-CD38 antibody is provided as a lyophilized formulation, wherein prior to administration, the lyophilized formulation is reconstituted forming a reconstituted antibody formulation such that the reconstituted antibody formulation has a pH of 6.2 and comprises the antibody at a concentration of about 50 mg/mL in a liquid comprising about 10 mM L-histidine, about 8% w/v sucrose, and about 0.05% v/v polysorbate 80. In some embodiments, one or more doses of an anti-CD38 antibody is provided as a lyophilized formulation, wherein prior to administration, the lyophilized formulation is reconstituted forming a reconstituted antibody formulation such that the reconstituted antibody formulation has a pH of 6.2 and comprises the antibody at a concentration of 50 mg/mL in a liquid comprising 10 mM L-histidine, 8% w/v sucrose, and 0.05% v/v polysorbate 80.

In some embodiments one or more doses of antibody is administered to the patent. In some embodiments, the dose can be about 0.1, about 0.2, about 0.3, about 0.5, about 1.0, about 2.5, about 5, about 10, or about 20 mg/kg of the antibody. In some embodiments, the dose can be 0.1, 0.2, 0.3, 0.5, 1.0, 2.5, 5, 10, and 20 mg/kg of the antibody. In some embodiments the antibody is administered intravenously. In some embodiments, the antibody is administered subcutaneously.

Definitions

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se. In some embodiments, the term "about" signifies a stated value plus or minus 10% of said value; for example, "about 10 mg/kg" can encompass 9 to 11 mg/kg. In some embodiments, the term "about" signifies a stated value plus or minus 5% of said value; for example, "about 20 mg/kg" can encompass 19 to 21 mg/kg.

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

Examples have been set forth below for the purpose of illustration and to describe certain specific embodiments of the invention. However, the scope of the claims is not to be in any way limited by the examples set forth herein.

EXAMPLES

1. Antibody Design:

Fc-engineered anti-CD38 antibodies were generated having mutations in the Fc part of the antibody to enhance the affinity for the activating FcγRIIIa and FcγRIIa receptors on effector cells.

Two humanized heavy chains (HC) (SEQ ID NO: 5 and SEQ ID NO: 6) carry 14 and 10 mutations in the framework regions (compared to SEQ ID NO: 1) which result in an increase in *Homo sapiens* germinality score from 74.49% to 88.78% and 84.69%, respectively. Two humanized light chains (LC) (SEQ ID NO: 8 and SEQ ID NO: 9) carry 17 and 15 mutations in the framework regions (compared to SEQ ID NO: 7) which result in an increase in *Homo sapiens* germinality score from 64.36% to 81.19% and 79.21%, respectively. In addition, in LC 2 and 3, methionine at position 11 was substituted with leucine to avoid a potential problematic methionine oxidation. The HC and LC sequences are provided in Table 2, and the mAb HC and LC pairings are provided in Table 3.

TABLE 2

| SEQ ID NO: | CHAIN | AMINO ACID SEQUENCE |
|---|---|---|
| 1 | HEAVY CHAIN 1 | QVQLVQSGAE VAKPGTSVKL SCKASGYTFT DYWMQWVKQR PGQGLEWIGT IYPGDGDTGY AQKFQGKATL TADKSSKTVY MHLSSLASED SAVYYCARGD YYGSNSLDYW GQGTSVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 2 | HEAVY CHAIN 2 | QVQLVQSGAE VAKPGTSVKL SCKASGYTFT DYWMQWVKQR PGQGLEWIGT IYPGDGDTGY AQKFQGKATL TADKSSKTVY MHLSSLASED SAVYYCARGD YYGSNSLDYW GQGTSVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PDVFLFPPKP KDTLMISRTP EVTCVVVDVS HEDPEVKFNW YVDGVEVHNA KTKPREEQYN STYRVVSVLT VLHQDWLNGK EYKCKVSNKA LPAPEEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 3 | HEAVY CHAIN 3 | QVQLVQSGAE VAKPGTSVKL SCKASGYTFT DYWMQWVKQR PGQGLEWIGT IYPGDGDTGY AQKFQGKATL TADKSSKTVY MHLSSLASED SAVYYCARGD YYGSNSLDYW GQGTSVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLAG PDVFLFPPKP KDTLMISRTP EVTCVVVDVS HEDPEVKFNW YVDGVEVHNA KTKPREEQYN STYRVVSVLT VLHQDWLNGK EYKCKVSNKA LPAPEEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 4 | HEAVY CHAIN 4 | QVQLVQSGAE VAKPGTSVKL SCKASGYTFT DYWMQWVKQR PGQGLEWIGT IYPGDGDTGY AQKFQGKATL TADKSSKTVY MHLSSLASED SAVYYCARGD YYGSNSLDYW GQGTSVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLAG PDVFLFPPKP KDTLMISRTP EVTCVVVDVS HEDPEVKFNW YVDGVEVHNA KTKPREEQYN STYRVVSVLT VLHQDWLNGK EYKCKVSNKA LPLPEEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 5 | HEAVY CHAIN 5 | QVQLVQSGAE VAKPGASVKV SCKASGYTFT DYWMQWVRQA PGQGLEWIGT IYPGDGDTSY AQKFQGRVTM TADTSTSTVY MELSSLRSED TAVYYCARGD YYGSNSLDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLAG PDVFLFPPKP KDTLMISRTP EVTCVVVDVS HEDPEVKFNW YVDGVEVHNA KTKPREEQYN STYRVVSVLT VLHQDWLNGK EYKCKVSNKA LPAPEEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 6 | HEAVY CHAIN 6 | QVQLVQSGAE VAKPGASVKV SCKASGYTFT DYWMQWVKQR PGQGLEWIGT IYPGDGDTGY AQKFQGRVTM TADTSTSTVY MELSSLRSED TAVYYCARGD YYGSNSLDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLAG PDVFLFPPKP KDTLMISRTP EVTCVVVDVS HEDPEVKFNW YVDGVEVHNA KTKPREEQYN STYRVVSVLT VLHQDWLNGK EYKCKVSNKA LPAPEEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 7 | LIGHT CHAIN 1 | DIVMTQSHLS MSTSLGDPVS ITCKASQDVS TVVAWYQQKP GQSPRRLIYS ASYRYIGVPD RFTGSGAGTD FTFTISSVQA EDLAVYYCQQ HYSPPYTFGG GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |

TABLE 2-continued

| SEQ ID NO: | CHAIN | AMINO ACID SEQUENCE |
|---|---|---|
| 8 | LIGHT CHAIN 2 | DIVMTQSPDS LAVSLGERAT INCKSSQDVS TVLAWYQQKP GQSPRRLIYS ASYRYIGVPD RFSGSGSGTD FTLTISSLQA EDVAVYYCQQ HYSPPYTFGG GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 9 | LIGHT CHAIN 3 | DIVMTQSPDS LAVSLGERAT INCKSSQDVS TVVAWYQQKP GQSPRRLIYS ASYRYIGVPD RFSGSGSGTD FTFTISSLQA EDVAVYYCQQ HYSPPYTFGG GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 10 | HEAVY CHAIN 7 | QVQLVQSGAE VAKPGTSVKL SCKASGYTFT DYWMQWVKQR PGQGLEWIGT IYPGDGDTGY AQKFQGKATL TADKSSKTVY MHLSSLASED SAVYYCARGD YYGSNSLDYW GQGTSVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 11 | huCD16a (FcγRIIIa) UniProtKB/ Swiss-Prot P08637 "158V" variant bold | MWQLLLPTAL LLLVSAGMRT EDLPKAVVFL EPQWYRVLEK DSVTLKCQGA YSPEDNSTQW FHNESLISSQ ASSYFIDAAT VDDSGEYRCQ TNLSTLSDPV QLEVHIGWLL LQAPRWVFKE EDPIHLRCHS WKNTALHKVT YLQNGKGRKY FHHNSDFYIP KATLKDSGSY FCRGLVGSKN VSSETVNITI TQGLAVSTIS SFFPPGYQVS FCLVMVLLFA VDTGLYFSVK TNIRSSTRDW KDHKFKWRKD PQDK |
| 12 | huFcγRIIa UniProtKB/ Swiss-Prot P12318-1 "131H" variant bold | MTMETQMSQN VCPRNLWLLQ PLTVLLLLAS ADSQAAAPPK AVLKLEPPWI NVLQEDSVTL TCQGARSPES DSIQWFHNGN LIPTHTQPSY RFKANNNDSG EYTCQTGQTS LSDPVHLTVL SEWLVQTPH LEFQEGETIM LRCHSWKDKP LVKVTFFQNG KSQKFSHLDP TFSIPQANHS HSGDYHCTGN IGYTLFSSKP VTITVQVPSM GSSSPMGIIV AVVIATAVAA IVAAVVALIY CRKKRISANS TDPVKAAQFE PPGRQMIAIR KRQLEETNND YETADGGYMT LNPRAPTDDD KNIYLTLPPN DHVNSNN |
| 13 | HEAVY CHAIN 8 | EVQLLESGGG LVQPGGSLRL SCAVSGFTFN SFAMSWVRQA PGKGLEWVSA ISGSGGGTYY ADSVKGRFTI SRDNSKNTLY LQMNSLRAED TAVYFCAKDK ILWFGEPVFD YWGQGTLVTV SSASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKRV EPKSCDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR EEMTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 14 | LIGHT CHAIN 4 | EIVLTQSPAT LSLSPGERAT LSCRASQSVS SYLAWYQQKP GQAPRLLIYD ASNRATGIPA RFSGSGSGTD FTLTISSLEP EDFAVYYCQQ RSNWPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |

TABLE 3

| mAb | Heavy Chain SEQ ID NO: | Light Chain SEQ ID NO: |
|---|---|---|
| 1 | 1 | 7 |
| 2 | 2 | 7 |
| 3 | 3 | 7 |
| 4 | 4 | 7 |
| 5 | 5 | 8 |
| 6 | 5 | 9 |
| 7 | 6 | 8 |
| 8 | 6 | 9 |
| 9 | 10 | 7 |
| 10 | 13 | 14 |

2. Biochemical Characterization:

A: Binding to CD38

In one experiment, binding affinity and kinetic constants of mAbs 1-8 for human CD38 was measured by SPR using a Biacore® instrument. Briefly, anti-CD38 antibodies were captured to a CM5 chip to which anti-Fc antibody had been covalently bound. Multiple concentrations of huCD38 were injected over the captured antibodies being tested. Binding curves (sensorgrams) were generated and kinetic analyses were performed using the Biacore Evaluation software.

As shown in Table 4, mAbs 3 and 8 had the highest affinity for human CD38 (T-tests for each variant: p-value >2).

TABLE 4

Affinity for human CD38 (n = 3)

| mAb | ka (1/Ms) | CV ka (%) | kd (1/s) | CV kd (%) | KD (M) | CV Kd (%) |
|---|---|---|---|---|---|---|
| 1 | 3.55E+06 | 11.6 | 6.55E−04 | 3.4 | 1.80E−10 | 5.0 |
| 3 | 3.89E+06 | 13.8 | 6.59E−04 | 2.2 | 1.71E−10 | 13.1 |
| 5 | 2.78E+06 | 11.0 | 1.88E−03 | 29.1 | 6.99E−10 | 22.1 |
| 6 | 3.10E+06 | 15.8 | 8.55E−03 | 76.2 | 3.85E−10 | 18.7 |
| 7 | 3.18E+06 | 15.4 | 1.30E−03 | 9.5 | 4.15E−10 | 14.5 |
| 8 | 3.51E+06 | 19.2 | 6.50E−04 | 4.7 | 1.91E−10 | 24.0 |

In another experiment, binding affinity of mAbs 1 and 3 to human CD38 was measured by SPR using a Biacore® instrument as described above. mAb 1 has a Kd of 0.22 nM and mAb 3 had a Kd of 0.20 nM.

Effect of thermal stress on the binding affinity to human CD38: Binding affinity and kinetic constants of mAbs 1-8 for human CD38 after subjecting the mAbs to thermal stress (14 days at 40° C. in 10 mM histidine pH6, 8% sucrose, 0.02% PS80) was measured by SPR using a Biacore® instrument. Same protocol described in the paragraph above has been used.

As shown in Table 5, the thermally stressed samples showed very similar affinity and kinetic constants as the corresponding non-stressed samples CD38 (Table 4) (T-tests for each variant: p-value >2).

TABLE 5

Effect of thermal stress on affinity for human CD38 (n = 3)

| mAb | ka (1/Ms) | CV ka (%) | kd (1/s) | CV kd (%) | KD (M) | CV KD (%) |
|---|---|---|---|---|---|---|
| 1 | 4.00E+06 | 21.9 | 7.14E−04 | 5.5 | 1.83E−10 | 15.7 |
| 3 | 3.71E+06 | 8.2 | 6.71E−04 | 3.0 | 1.81E−10 | 5.3 |
| 5 | 2.95E+06 | 21.2 | 2.36E−03 | 4.4 | 8.28E−10 | 25.7 |
| 6 | 3.86E+06 | 27.9 | 1.28E−03 | 3.7 | 3.46E−10 | 24.0 |
| 7 | 3.39E+06 | 6.8 | 1.33E−03 | 5.9 | 3.94E−10 | 10.5 |
| 8 | 3.53E+06 | 25.2 | 6.63E−04 | 11.7 | 1.98E−10 | 31.5 |

B: Measurement of affinity for FcγRIIa, FcγRIIIa, and FcγRIIIb in silico

In one experiment, affinity of the mAbs for FcγRIIIa 158V receptors or FcγRIIIa 158F receptors was measured using Surface Plasmon Resonance (SPR). The mAbs were produced in HEK293 cells by transient transfection according to supplier (ThermoFisher Scientific), and purified by protein A affinity chromatography according to supplier (GE Healthcare). FcγRIIIa (CD16a) extracellular domains with V158 or F158 were produced with a C-terminal histag in HEK293 cells by transient expression and purified by Immobilized Metal Affinity Chromatography (IMAC) according to the supplier (Ni-Sepharose GE, Healthcare). Affinity by SPR on BIACore 2000 (GE Healthcare) was performed by capture assay using immobilized anti-His IgG on CM5 chip. FcγRIIIa-histag was then added to the running buffer, followed afterwards by the anti-CD38 mAb at concentrations ranging from 8 to 256 nM. Analysis was performed using the two-state reaction with acceptable $\chi^2$ values of less than 5 (meaning 2% of the highest tested concentration) and a percentage of maximal theoretical resonance unit greater than 25 (meaning more than ¼ productive interaction), using BIAevaluation Software 4_1 (GE Healthcare).

As shown in Table 6, mAbs 2-4 have a 9-fold higher affinity for the FcγRIIIa 158V than mAb 1 and more than 27-fold higher affinity for the FcγRIIIa 158F receptor than mAb 1.

TABLE 6

| mAb | $K_D$ (nM) | |
|---|---|---|
| | FcγRIIIa 158V | FcγRIIIa 158F |
| 1 | 425 | >1500 |
| 2 | 47 | 53 |
| 3 | 50 | 55 |
| 4 | 47 | 51 |

In another experiment, the affinity of mAbs 1 and 3 for FcγRIIIa 158V receptors or FcγRIIIa 158F receptors was measured using SPR as described above. mAb 3 bound FcγRIIIa 158V with a KD of 75 nM, and mAb 3 bound FcγRIIIa 158F with a KD of 59 nM.

The affinity of the mAbs for FcγRIIa receptors having arginine at amino acid position 131 (FcγRIIa 131R) or histidine at amino acid position 131 (FcγRIIa 131H) was measured using AlphaScreen proximity assay.

FcγRIIa extracellular domains with R131 or H131 were provided by R&D System (batch 1330-CD) or Biorbyt (batch ORB138408), respectively. The assay was a bead based proximity assay described by supplier (Perkin Elmer), permitting a ranking of the anti-CD38 Fc variants by competition to anti-CD38 with native IgG1. Biotinylated-anti-CD38 with native IgG1 was captured on the donor beads, and FcγRIIa histag-protein was captured on the acceptor beads. When anti-CD38 and FcγRIIa interact, beads are brought into proximity. Excitation of the donor beads at 680 nm causes the release of singlet oxygen, which diffuses and triggers the emission of light at 520-620 nm from the acceptor beads, when in proximity. The amount of light is directly proportional to the degree of interaction and it is measured with the EnVision multimode plate reader (Perkin Elmer). During the competition assay, the untagged competitive mAbs anti-CD38 Fc-variants DE (S239D/I332E, Eu numbering), ADE (G236A/S239D/I332E, Eu numbering), or ADLE (G236A/S239D/F243L/I332E, Eu numbering) were used to compete the interaction between the biotinylated-anti-CD38 with native IgG1 and FcγRIIa-histag protein. The concentration of biotinylated-anti-CD38 was set from a calibration curve performed in advance. The untagged competitive mAbs were used at varying levels such that increasing concentration of untagged mAbs can displace the biotinylated anti-CD38 and decreases the signal. Data were normalized for maximal signal. Two experiments were run and IC50 evaluated by BIOST@T-SPEED-LTS 2.1.0.

As shown in Table 7, mAb 3 showed greater than 14- and 18-fold higher affinity for FcγRIIa 131R and FcγRIIa 131H, respectively, compared to mAb 1.

TABLE 7

Affinity to FcγRIIa R131 and FcγRIIa H131

| mAb | Relative IC50 (nM) | |
|---|---|---|
| | FcγRIIa R131 | FcγRIIa H131 |
| 1 | 1741 | 268 |
| 2 | 687 | 119 |
| 3 | 125 | 15 |
| 4 | 508 | 58 |

C: Measurement of Affinity for FcγRIIa, FcγRIIIa, and FcγRIIb In Vitro

HEK293T-FcγRIIIa-158F, HEK293T-FcγRIIIa-158V, HEK293T-FcγRIIa-131H, HEK293T-FcγRIIa-131R,

HEK293T-FcγRI or HEK293T-FcγRIIb were seeded in 96-well microplates at $10^5$ cells/well. The plates were centrifuged at 800 g for 1 minute and resuspended in 50 μL PBS containing the antibodies at different concentrations for 30 minutes at 4° C. 200 μL PBS 1% FBS was then added to wash the cells, followed by a 800 g centrifugation for 1 minute. The washing step was repeated three times in total before staining the cells with the secondary antibody conjugated with FITC (Fragment Goat Anti-human IgG (H+L) FITC, ref 109-546-088 Jackson ImmunoResearch, 10 μg/mL final) for 30 minutes at 4° C. Cells were washed with 200 μL PBS 1% FBS three times and resuspended in 100 μL PBS before acquisition on MACSVYB (B1 channel). As shown in Table 8, mAb 2, 3 and 4 had a 32-, 38-, and 51-fold higher affinity for FcγRIIIa 158F expressed on HEK cells compared to mAb 1, respectively, and mAb 2, 3 and 4 had a 9-, 5-, and 6-fold higher affinity for FcγRIIIa 158V expressed on HEK cells compared to mAb 1, respectively.

TABLE 8

| | mAb | Mean apparent Kd (nM) | SEM | Fold difference in affinity versus mAb 1 |
|---|---|---|---|---|
| FcγRIIIa 158F | 1 | 2269.1 | 771.4 | 1 |
| | 2 | 70.1 | 13.1 | 32.4 |
| | 3 | 60.4 | 10.4 | 37.6 |
| | 4 | 44.2 | 9.1 | 51.4 |
| FcγRIIIa 158V | 1 | 165.3 | 44.2 | 1 |
| | 2 | 17.6 | 3.3 | 9.4 |
| | 3 | 32.0 | 5.3 | 5.2 |
| | 4 | 28.1 | 7.8 | 5.9 |

As shown in Table 9, mAb 3 had a ~5-fold higher affinity for FcγRIIa 131H expressed on HEK cells compared to mAb 1, and mAb 3 had a ~16-fold higher affinity for FcγRIIa 131R expressed on HEK cells compared to mAb 1.

TABLE 9

| | mAb | Mean Kd (nM) | SEM | difference in affinity versus mAb 1 |
|---|---|---|---|---|
| FcγRIIa 131H | 1 | 1180.8 | 406.1 | 1 |
| | 2 | 839.8 | 438.7 | 1.4 |
| | 3 | 221.9 | 74.9 | 5.3 |
| | 4 | 543.8 | 277.7 | 2.2 |
| FcγRIIa 131R | 1 | 1420.3 | 166.5 | 1 |
| | 2 | 891.1 | 131.1 | 1.6 |
| | 3 | 87.4 | 13.9 | 16.3 |
| | 4 | 467.3 | 153.6 | 3.0 |

As shown in Table 10, mAb 2, 3 and 4 had a similar level of binding affinity for FcγRI compared to mAb 1 and a 1.8- to 3.9-fold lower affinity for FcγRIIb expressed on HEK cells compared to mAb 1.

TABLE 10

| | mAb | Mean Kd (nM) | SEM | difference in affinity versus mAb 1 |
|---|---|---|---|---|
| FcγRI | 1 | 24.2 | 4.2 | 1 |
| | 2 | 13.5 | 1.7 | 1.8 |
| | 3 | 14.7 | 3.2 | 1.6 |
| | 4 | 15.9 | 2.7 | 1.5 |
| FcγRIIb | 1 | 1299.1 | 406.1 | 1 |
| | 2 | 839.8 | 438.7 | 3.9 |
| | 3 | 221.9 | 74.9 | 3.3 |
| | 4 | 543.8 | 277.7 | 1.8 |

D: Measurement of Cytotoxic Activities In Vitro

Antibody Dependent Cellular Cytotoxicity (ADCC):

Antibody Dependent Cell Cytotoxic (ADCC) assays using NK92 cell line engineered to over-express the FcγRIIIa receptor as effector cells were examined using a calcein-acetyoxymethyl (Calcein-AM; Invitrogen) release assay. In live cells, the non-fluorescent calcein AM is converted to a green-fluorescent calcein. The labeled target cells are incubated with SAR442085 antibody and the NK-92 effector cells. Lysis of the target cells through ADCC leads to release of the fluorescent calcein. The intensity of fluorescence is proportional to the level of ADCC activity present.

The multiple myeloma target cells (MOLP-8, RPMI 8226, MM1R or KMS12-BM) were labeled with Calcein-AM (50 μg diluted in 25 μL DMSO, then diluted 10 μL calcein in 4 mL RPMI 1640+1% FBS+1% Probenecid for staining of $4 \times 10^6$ cells) for 30 min, then washed and plated onto 96-well round bottom plates at a density of $2 \times 10^4$ cells/well. The indicated test mAbs or control isotype mAb were added at various concentrations from 10 μg/mL to 0.01 μg/mL for 30 min to allow opsonization before adding Natural Killer (NK) cells transduced with the indicated FcγRIIIa variant. NK cells expressing 158F or 158V were added as effector cells at an E:T ratio of 5:1 ($1 \times 10^5$ NK cells for $2 \times 10^4$ target cells). The plates were then incubated for 1 h at 37° C. in a humidified incubator with 5% $CO_2$, and 100 μL of supernatants were harvested and transferred into opaque 96-well microplates for analysis using fluorometry on Tecan Infinite M1000 to measure calcein release (excitation filter: 492 nm; emission: 515 nm). For maximal release, the cells were lysed with 2% Triton X-100. The fluorescence value of the culture medium background was subtracted from that of the experimental release (A), the target cell spontaneous release (B), and the target cell maximal release (C). The cytotoxicity and ADCC percentages for each plate (in duplicate) were calculated using the following formula:

Cytotoxicity (%)=$(A-B)/(C-B) \times 100\%$

Each experiment was repeated at least 3 times. The half-maximal effective concentration (EC50) values were calculated by fitting the data points to a 4-parameter equation using GraphPad Prism 5 (GraphPad Software, Inc., San Diego, Calif.).

High CD38 Receptor Density Target Cells

ADCC of multiple myeloma cell line MOLP-8 was assessed in vitro as described above. MOLP-8 cells exhibit a high CD38 receptor density on the cell surface (~400,000/cell).

Table 11 shows EC50 of each tested antibody against MOLP-8 cells in the presence of NK cells expressing 158V. As shown in Table 11, in the presence of NK cells expressing the high affinity variant of FcγRIIIa (158V), mAbs 2, 3, and 4 triggered ADCC of MOLP-8 cells with an EC50 of 24- to 33-fold lower than mAb 1.

TABLE 11

| mAb | EC50 (ng/ml) | SEM (ng/ml) |
| --- | --- | --- |
| 1 | 3.3 | 0.91 |
| 2 | 0.1 | 0.03 |
| 3 | 0.14 | 0.02 |
| 4 | 0.12 | 0.02 |

Table 12 shows EC50 of each tested antibody against MOLP-8 cells in the presence of NK cells expressing 158F. As shown in Table 12, mAb 4 showed the strongest ADCC activity against MOLP-8 cells in the presence of NK cells expressing the low affinity FcγRIIIa variant (158F), with and EC50 of about 97-fold lower than mAb 1. mAbs 2 and 3 triggered ADCC of MOLP-8 cells with an EC50 of about 59- to 69-fold lower than mAb 1 in the presence of NK cells expressing the low affinity FcγRIIIa variant (158F).

TABLE 12

| mAb | EC50 (ng/ml) | SEM (ng/ml) |
| --- | --- | --- |
| 1 | 16.5 | 8.77 |
| 2 | 0.24 | 0.11 |
| 3 | 0.28 | 0.09 |
| 4 | 0.17 | 0.05 |

Medium CD38 Receptor Density Target Cells

ADCC of multiple myeloma cell line RPMI-8226 was assessed in vitro as described above. RPMI-8226 cells exhibit a medium CD38 receptor density on the cell surface (~70,000/cell).

Table 13 shows EC50 of each tested antibody against RPMI-8226 cells in the presence of NK cells expressing 158V. As shown in Table 13, mAbs 2-4 demonstrated similar levels of enhanced ability with an EC50 of about 27-fold lower compared to mAb 1 to trigger ADCC against MM cells expressing a medium CD38 receptor density in the presence of NK cells expressing the higher affinity variant of FcγRIIIa (158V).

TABLE 13

| mAb | EC50 (ng/ml) | SEM (ng/ml) |
| --- | --- | --- |
| 1 | 2.45 | 0.73 |
| 2 | 0.09 | 0.02 |
| 3 | 0.09 | 0.003 |
| 4 | 0.09 | 0.003 |

Table 14 shows EC50 of each tested antibody against RPMI-8226 cells in the presence of NK cells expressing 158F. mAb 4 demonstrated about a 73-fold enhanced ability compared to mAb 1 to trigger ADCC against MM cells expressing a medium CD38 receptor density in the presence of NK cells expressing the low affinity variant of FcγRIIIa, while mAb 3 demonstrated about a 65-fold and mAb 2 demonstrated about a 49-fold enhanced ability to trigger ADCC against MM cells expressing a medium CD38 receptor density in the presence of NK cells expressing the low affinity variant of FcγRIIIa compared to mAb 1.

TABLE 14

| mAb | EC50 (ng/ml) | SEM (ng/ml) |
| --- | --- | --- |
| 1 | 5.83 | 1.67 |
| 2 | 0.12 | 0.04 |
| 3 | 0.09 | 0.01 |
| 4 | 0.08 | 0.01 |

Low CD38 Receptor Density Target Cells

ADCC of multiple myeloma cell line KMS-12BM was assessed in vitro as described above. KMS-12BM cells exhibit a low CD38 receptor density on the cell surface (~13,000/cell).

Table 15 shows EC50 of each tested antibody against KMS-12BM cells in the presence of NK cells expressing the higher affinity variant of FcγRIIIa (158V). Interestingly, as shown in Table 15, mAbs 2, 3, and 4 demonstrated enhanced ability compared to mAb 1 to trigger ADCC against MM cells expressing a low CD38 receptor density in the presence of NK cells expressing the higher affinity variant of FcγRIIIa (158V). mAb 3 had an EC50 of ~69-fold lower than mAb 1, and mAb 4 had an EC50 of ~91-fold lower than mAb 1.

TABLE 15

| mAb | EC50 (ng/ml) | SEM (ng/ml) |
| --- | --- | --- |
| 1 | 41 | 12 |
| 2 | 0.65 | 0.05 |
| 3 | 0.6 | 0.1 |
| 4 | 0.45 | 0.35 |

Table 16 shows EC50 of each tested antibody against KMS-12BM cells in the presence of NK cells expressing the lower affinity variant of FcγRIIIa (158F). Remarkably, as shown in Table 16, mAbs 2, 3, and 4 demonstrated enhanced ability to trigger ADCC compared to mAb 1 against MM cells expressing a low CD38 receptor density in the presence of NK cells expressing the lower affinity variant of FcγRIIIa (158F). mAb 3 had an EC50 of ~145-fold lower than mAb 1, and mAb 4 had an EC50 of ~269-fold lower than mAb 1.

TABLE 16

| mAb | EC50 (ng/ml) | SEM (ng/ml) |
| --- | --- | --- |
| 1 | 94 | 2.55 |
| 2 | 1.05 | 0.25 |
| 3 | 0.65 | 0.15 |
| 4 | 0.35 | 0.15 |

Antibody Dependent Cellular Phagocytosis (ADCP):

Human PBMCs were first isolated from buffy coat of seven healthy donors from Etablissement Français du Sang. All these donors exhibited the same FCGR3A and FCGR2A genotype (FcγRIIIa-158V/V and FcγRIIa-131H/H). Blood was first collected in a 50 mL Falcon tube. 15 mL of Ficoll-Plaque™ PLUS 96% was added very gently at the bottom of a Sepmate tube, then blood added slowly in the tube before centrifugation at 1,300 g for 10 minutes. The PBMC ring was then collected and washed with 50 mL PBS and another round of centrifugation at 300 g for 5 minutes. The washing process was repeated two times before PBMC staining with anti-CD14 magnetic beads according to manufacturer's instructions (Miltenyi; ref 130-050-201): basically an incubation time at 4° C. for 15 minutes before positive selection through the AutoMACS pro (Posseld selection). Monocytes were collected and then washed with 50 mL PBS. Monocytes were cultured for 5 days in RPMI1640, 10% FBS, 2% human inactivated serum, 50 ng/ml GM-CSF in a T75 flask at 37° C. 5% $CO_2$. After 5 days culture, monocytes were differentiated into macrophages. To collect macrophages, accutase (ThermoFisher, ref: A1110501) was put in flasks for 15 minutes at 37° C. to detach cells, then 20 mL RPMI 10% FBS 1% Glutamine was added to stop accutase activity. Collected cells were centrifuged at 350 g for 10 minutes followed by a wash in 20 mL PBS and another round of centrifugation at 300 g for 10 minutes. For two experiments, the macrophages used were from a macrophage batch frozen in liquid nitrogen.

Macrophages were resuspended in diluent C at $20 \times 10^6$ cells/mL (provided in manufacturer's staining kit #PKH26GL-1KT from Sigma Aldrich). For 1 volume of macrophages, 1 volume of PKH26 (20 µL diluted in 1 mL diluent C) was added to the cells for 5 minutes incubation in the dark. 5 mL FBS were then added to inactivate the staining process for 1 minute, before completing to 50 mL with RPMI1640 10% FBS.CD38-expressing MOLP-8 cells were stained with PKH67 fluorochrome and macrophages derived from purified monocytes were stained with PKH26, making them distinguishable by flow cytometry. Then MOLP-8 cells and macrophages were put in culture in the presence of either mAb 1 or mAb 3 overnight before analysis of the double positive population (macrophages that phagocytosed MOLP-8 cells) by flow cytometry.

mAb 3 exhibited an enhanced ADCP activity as compared to mAb 1 against MOLP-8 cell line as demonstrated by the higher percentage (%) of total phagocytosis achieved in all experiments and the lower EC50 (relative) value (EC50rel). The geometric mean of the % of total phagocytosis was 40.85% for mAb 3 versus 18.57% for mAb 1 and the geometric mean of EC50rel was 31.87 ng/mL (or 212.57 pM) for mAb 3 versus mAb 1 for which the value was over 64.86 ng/mL (or over 432.62 pM). Based on EC50rel values, mAb 3 appeared to be at least 2.035 times better than mAb 1 for the ADCP activity.

In Vivo Efficacy

The in vivo efficacy of mAb 3 was evaluated. Humanized FcγR C57BL/6 mice (Smith P, DiLillo D J, Bournazos S, Li F, Ravetch J V; Proc Natl Acad Sci USA. 2012; 109(16): 6181-6) were injected intravenously with 500,000 EL4-huCD38 tumor cells on day 0. Humanized FcγR C57BL/6 mice have had all murine genes encoding FcγRs deleted and human FcγRs, encoded as transgenes, inserted into the mouse genome. Humanized FcγR C57BL/6 mice recapitulate huFcγR expression patterns and expression levels and are functional in a variety of huIgG-mediated models of inflammation, cytotoxicity, and tumor clearance. For the activating FcγRIIIa and FcγRIIa receptors, the human variants inserted in the mouse model were, respectively, huFcγRIIIa 158F and huFcγRIIa 131R (the low affinity variants of the receptors). The profile of human FcγR expression pattern and expression levels were recapitulated in the mouse.

Starting on day 1 post tumor cell injection, the test or control mAbs were administered intraperitoneally on days 1, 4, 7, and 14. The isotype control mAb was administered at 10 mg/kg. mAbs 1, 3, and 10 were administered at 10 and 1.25 mg/kg. In this survival model, the primary efficacy end points were Median Survival Time (MST), the percent Increased Lifespan (% ILS), and the long term survivors (defined as mice with survival duration superior or equal to 2 times the MST of control group). The survival differences between groups were evaluated with a Cox model.

As shown in Table 17, the isotype control group had an MST of 39 days. Twenty percent of the isotype control group exhibited long term survival with this model. The group treated with mAb 1 at 10 mg/kg had a MST of more than 82.5 days, an increased lifespan greater than 112%. Fifty percent of the group treated with 10 mg/kg of mAb 1 was long term survivors. Mice treated with 1.25 mg/kg of mAb 1 had an MST greater than 46.5 days, and an increased lifespan greater than 19%. Thirty percent of the group treated with 1.25 mg/kg of mAb 1 was long term survivors.

The group treated with mAb 10 at 10 mg/kg had a MST of more than 70 days, an increased lifespan of 70%. Fifty percent of the group treated with 10 mg/kg of mAb 10 was long term survivors. Mice treated with 1.25 mg/kg of mAb 10 had an MST greater than 42 days, and an increased lifespan of 8%. Only 10% of the group treated with 1.25 mg/kg of mAb 10 was long term survivors.

The group treated with mAb 3 at 10 mg/kg had a MST of more than 90 days, an increased lifespan greater than 131%. Remarkably, 90% of the group treated with 10 mg/kg of mAb 3 was long term survivors. mAb 3 at 10 mg/kg was statistically significantly more active compared to the isotype control group (p=0.0351). Even more surprising, mice treated with 1.25 mg/kg of mAb 3 also had an MST greater than 90 days, and an increased lifespan greater than 131%. Furthermore, 90% of the group treated with 1.25 mg/kg of mAb 3 was long term survivors. mAb 3 at 1.25 mg/kg was statistically significantly more active as compared to the isotype control group (p=0.0380) and statistically significantly better than mAb 10 at the same dose (p=0.0380).

Treatment of this tumor model in mice bearing the low affinity huFcγRIIIa (F158/F158) with mAb 1, mAb 3, and mAb 10 at the dose of 10 mg/kg resulted in a statistically significant improvement in lifespan and number of long term survivors. Surprisingly, however, at the dose of 1.25 mg/kg, mAb 3 still exhibited a statistically significant improvement in lifespan and number of long term survivors while mAb 1 and mAb 10 were inactive.

TABLE 17

| Agent | Dosage (mb/kg) | Long term survivors (%) | MST (day) | % ILS |
|---|---|---|---|---|
| Isotype control | 10 | 20 | 39 | — |
| mAb 3 | 10 | 90 | >90 | 131% |
|  | 1.25 | 90 | >90 | 131% |
| mAb 1 | 10 | 50 | 82.5 | 112% |
|  | 1.25 | 30 | 46.5 | 19% |
| mAb 10 | 10 | 50 | 70 | 79% |
|  | 1.25 | 10 | 42 | 8% |

E. Stability Studies

Thermostability

The thermostability of mAbs 1, 3, 5, 6, 7, and 8 was measured by differential scanning calorimetry (DSC) using a Malvern MicroCal VP calorimeter. The samples were tested in a buffer comprising 10 mM histidine HCl at pH 6.0. The prepared samples were loaded into wells of a Wheaton 96-well round bottom plate, along with buffer as reference, in triplicate. Using a temperature ramp rate of 1° C./min and a range of 20-120° C., thermal scans were collected and processed using origin software 2.0.

As shown in Table 18, mAbs 3, 5, 6, 7, and 8 showed an onset of protein conformation change at about 40° C., at a temperature of about 17 degrees lower than the onset temperature of mAb 1 and 15-20° C. lower than is typical for mAbs (FIG. 1). Furthermore, unfolding of the CH2 domain of mAbs 3, 5, 6, 7, and 8 began much earlier than for mAb 1, at about 50° C. compared to 70° C.

TABLE 18

| | | Thermostability (° C.) | | | |
|---|---|---|---|---|---|
| mAb | $T_{onset}$ | Tm1 (CH2) | Tm2 (Fab1) | Tm3 (Fab2) | Tm4 (CH3) |
| 1 | 56.8 | | 70.0 | 75.7 | 83.1 |
| 3 | 39.9 | 50.4 | 71.0 | | 83.3 |
| 5 | 37.8 | 49.9 | 79.4 | | 81.9 |
| 6 | 40.7 | 49.8 | 81.7 | | 84.1 |
| 7 | 37.2 | 50.0 | 78.1 | | 84.3 |
| 8 | 38.8 | 50.5 | 80.2 | | 84.8 |

Isoelectric Point

The isoelectric point (pI) of each of mAbs 1, 3, 5, 6, 7, and 8 was measured by capillary isoelectric focusing (cIEF). The theoretical pIs were determined from composition using the analysis platform SEDNTERP and assuming the following amino acid pKa values: Arg=12, Asp=4.5, Glu=4.6, His=6.2, Lys=10.4, and Tyr=9.7. All sulfhydryl sidechains in Cys residues were assumed disulfide-bonded with no contributing pKa (Laue™, Shah BD, Ridgeway™, and Pelletier SL. Computer-aided interpretation of analytical sedimentation data for protein. In Analytical Ultracentrifugation in Biochemistry and Polymer Science. Harding S E, Rowe A J, and Horton J C Eds. pp 90-124. Royal Society of Chemistry, 1991).

Surprisingly, as shown in Table 19, the measured pI was lower than the calculated pI for mAb 3 based on the sequence.

TABLE 19

| mAb | Calculated pI | Measured pI | % "acidic" forms | % "basic" forms |
|---|---|---|---|---|
| 1 | 7.46 | 7.47 | 16.6 | 19.0 |
| 3 | 7.46 | 6.95 | 20.1 | 44.0 |
| 5 | 6.72 | 5.67 | 20.7 | 23.6 |
| 6 | 6.72 | 5.66 | 16.8 | 21.5 |
| 7 | 7.11 | 6.01 | 25.8 | 48.5 |
| 8 | 7.11 | 6.22 | 11.5 | 25.7 |

Formulation Development of mAb 3

Based on the thermostability results, a lyophilized formulation was developed to ensure adequate stability of mAb 3 that was suitable for storage of the mAb at ≤−30° C. and for storage of the lyophilized mAb at 2-8° C. mAb 3 formulations using different buffering systems and at different pHs were tested in stability studies comprised of freeze-thaw cycling, agitation studies, and short-term (12 weeks) incubation at stress, accelerated and intended storage conditions of 40° C., 25° C., 5° C., −30° C., and −80° C. In these experiments, aggregation and chemical degradation of the protein were evaluated in addition to particle formation (visual inspection, light obscuration-based particle counting, and micro-flow imaging).

Based on results from formulation development studies, a formulation containing 10 mM L-histidine-HCl, 8% w/v sucrose, and 0.05% w/v polysorbate 80, pH 6.2 was chosen.

Lyophilization Process Development

A lyophilization process was developed for mAb 3 to ensure that the formulated antibody had acceptable stability and cake attributes following lyophilization. Process parameters of the lyophilization cycle (drying temperatures, chamber pressure, etc.) were determined based on a number of development runs using a lab scale lyophilizer (Genesis EL35 manufactured by SP Scientific). The robustness of the cycle was established by conducting a series of lyophilization runs with controlled excursions in freezing rate, drying temperatures and chamber vacuum pressure. The stability studies on lyophilized formulated antibody comprised of short-term (12 weeks) incubation at stress, accelerated and intended storage conditions of 40° C., 25° C., and 5° C. In these experiments, lyophilized powder attributes (cake appearance, reconstitution time, oxygen headspace, moisture content) were evaluated in addition to aggregation, chemical degradation, and particle formation. Based on formulation and lyophilization development studies, the composition of mAb 3 and was selected as 50 mg/mL mAb 3, 10 mM L-histidine-HCl, 8% w/v sucrose, 0.05% w/v polysorbate 80, and at a pH 6.2. The formulated antibody is stored at ≤−30° C. and lyophilized formulated antibody is stored at 2-8° C.

We claim:

1. An antibody that specifically binds human CD38, wherein the antibody comprises
   a) a heavy chain (HC) having an amino acid sequence of SEQ ID NO: 2 and a light chain (LC) having an amino acid sequence of SEQ ID NO: 7, or
   b) a heavy chain (HC) having an amino acid sequence of SEQ ID NO: 3 and a light chain (LC) having an amino acid sequence of SEQ ID NO: 7, or
   c) a heavy chain (HC) having an amino acid sequence of SEQ ID NO: 4 and a light chain (LC) having an amino acid sequence of SEQ ID NO: 7, or
   d) a heavy chain (HC) having an amino acid sequence of SEQ ID NO: 5 and a light chain (LC) having an amino acid sequence of SEQ ID NO: 8, or
   e) a heavy chain (HC) having an amino acid sequence of SEQ ID NO: 5 and a light chain (LC) having an amino acid sequence of SEQ ID NO: 9, or
   f) a heavy chain (HC) having an amino acid sequence of SEQ ID NO: 6 and a light chain (LC) having an amino acid sequence of SEQ ID NO: 8, or
   g) a heavy chain (HC) having an amino acid sequence of SEQ ID NO: 6 and a light chain (LC) having an amino acid sequence of SEQ ID NO: 9.

2. A pharmaceutical composition comprising a formulated antibody, wherein the formulated antibody comprises an antibody, sucrose, L-histidine, and polysorbate 80 (PS80), wherein the antibody specifically binds human CD38 and is present at a concentration of 50 mg/mL, the sucrose is present at a concentration of 8% (w/v), the L-histidine is present at a concentration of 10 mM, and the PS80 is present at a concentration of 0.05% (v/v), wherein the formulation has a pH of 6.2, and wherein the antibody comprises
- a) a heavy chain (HC) having an amino acid sequence of SEQ ID NO: 2 and a light chain (LC) having an amino acid sequence of SEQ ID NO: 7, or
- b) a heavy chain (HC) having an amino acid sequence of SEQ ID NO: 3 and a light chain (LC) having an amino acid sequence of SEQ ID NO: 7, or
- c) a heavy chain (HC) having an amino acid sequence of SEQ ID NO: 4 and a light chain (LC) having an amino acid sequence of SEQ ID NO: 7, or
- d) a heavy chain (HC) having an amino acid sequence of SEQ ID NO: 5 and a light chain (LC) having an amino acid sequence of SEQ ID NO: 8, or
- e) a heavy chain (HC) having an amino acid sequence of SEQ ID NO: 5 and a light chain (LC) having an amino acid sequence of SEQ ID NO: 9, or
- f) a heavy chain (HC) having an amino acid sequence of SEQ ID NO: 6 and a light chain (LC) having an amino acid sequence of SEQ ID NO: 8, or
- g) a heavy chain (HC) having an amino acid sequence of SEQ ID NO: 6 and a light chain (LC) having an amino acid sequence of SEQ ID NO: 9.

3. A unit dosage form of a formulated antibody that specifically binds human CD38, wherein the formulated antibody comprises 215 mg of the antibody, 6.21 mg L-histidine, 344 mg sucrose, and 2.15 mg polysorbate 80, wherein the formulated antibody is lyophilized, and wherein the antibody comprises
- a) a heavy chain (HC) having an amino acid sequence of SEQ ID NO: 2 and a light chain (LC) having an amino acid sequence of SEQ ID NO: 7, or
- b) a heavy chain (HC) having an amino acid sequence of SEQ ID NO: 3 and a light chain (LC) having an amino acid sequence of SEQ ID NO: 7, or
- c) a heavy chain (HC) having an amino acid sequence of SEQ ID NO: 4 and a light chain (LC) having an amino acid sequence of SEQ ID NO: 7, or
- d) a heavy chain (HC) having an amino acid sequence of SEQ ID NO: 5 and a light chain (LC) having an amino acid sequence of SEQ ID NO: 8, or
- e) a heavy chain (HC) having an amino acid sequence of SEQ ID NO: 5 and a light chain (LC) having an amino acid sequence of SEQ ID NO: 9, or
- f) a heavy chain (HC) having an amino acid sequence of SEQ ID NO: 6 and a light chain (LC) having an amino acid sequence of SEQ ID NO: 8, or
- g) a heavy chain (HC) having an amino acid sequence of SEQ ID NO: 6 and a light chain (LC) having an amino acid sequence of SEQ ID NO: 9.

4. The pharmaceutical composition of claim 2, wherein the formulated antibody is lyophilized.

5. The pharmaceutical composition of claim 2, wherein amino acid at position 1 of the HC amino acid sequence is pyroglutamine.

6. The pharmaceutical composition of claim 2, wherein the antibody has an isoelectric point (pI) of 5.8 to 9.0 when measured by capillary isoelectric focusing (cIEF).

7. The pharmaceutical composition of claim 2, wherein the antibody comprises a main charge variant and at least one acidic charge variant and wherein the antibody has at least one of
- a) the HC of the at least one charge variant comprises at least one deamidated asparagine selected from the group consisting of N289, N318, N387, and N392 as numbered according to SEQ ID NO: 1, or
- b) the antibody comprises a main charge variant and least one acidic charge variant, wherein the main charge variant comprises at least 71% of the antibody and the acidic charge variant comprises no more than 30% of the antibody, or
- c) the main charge variant has an isoelectric point (pI) of 7.5 and wherein the one or more acidic charge variant has pI of 5.8 when measured by capillary isoelectric focusing (cIEF).

8. The pharmaceutical composition of claim 2, wherein the antibody comprises at least one basic charge variant, and wherein the antibody has at least one of
- a) the basic charge variant comprises no more than 4% of the antibody, or
- b) the one or more basic charge variants has a pI of 9.0 when measured by capillary isoelectric focusing (cIEF).

9. The pharmaceutical composition of claim 2, wherein the antibody
- a) is capable of killing a CD38-expressing cell by Antibody Dependent Cellular Cytotoxicity (ADCC), wherein the cell has a CD38 receptor density of ≤13,000 CD38 sites on the surface of the cell in the presence of Natural Killer cells expressing the 158F, 158V, or both 158F and 158V variants CD16a (FcγRIIIa), and/or
- b) binds CD16a (FcγRIIIa) having phenylalanine at amino acid position 158 (158F) with a KD of 59 nM as measured by Surface Plasmon Resonance (SPR) and wherein the antibody binds CD16a having valine at amino acid position 158 (158V) with a KD of 75 nM as measured by SPR, and/or
- c) binds CD16a (FcγRIIIa) having phenylalanine at amino acid position 158 (158F) with a KD of 96 nM as measured by binding to FcγRIIIa 158F-expressing HEK cells and wherein the antibody binds FcγRIIIa having valine at amino acid position 158 (158V) with a KD of 40 nM as measured by binding to FcγRIIIa 158V-expressing HEK cells, and/or
- d) binds CD32a (FcγRIIa) having arginine at amino acid position 131 (131R) with a KD of 94 nM as measured by binding to FcγRIIa 131R-expressing HEK cells and wherein the antibody binds FcγRIIa having histidine at amino acid position 131 (131H) with a KD of 222 nM as measured by binding to FcγRIIa 131H-expressing HEK cells.

10. The pharmaceutical composition of claim 2, wherein
- a) the antibody is capable of killing a CD38-expressing cell by ADCC wherein the cell has a CD38 receptor density of >400,000 on the surface of the cell, and is capable of killing a CD38-expressing cell by ADCC wherein the cell has a CD38 receptor density of ≥100,000 on the surface of the cell, and is capable of killing a CD38-expressing cell by ADCC wherein the cell has a CD38 receptor density of ≤13,000 on the surface of the cell, in the presence of Natural Killer cells expressing the 158F, 158V, or both 158F and 158V variants of CD16a (FcγRIIIa) and/or
- b) the antibody is capable of killing a CD38-expressing cell by Antibody Dependent Cellular Phagocytosis (ADCP) in the presence of human peripheral blood mononuclear cells (PMBCs), wherein the cell has a CD38 receptor density of >400,000 on the surface of the cell.

11. The pharmaceutical composition of claim 10, wherein
a) in the presence of Natural Killer cells expressing the higher affinity variant (158V) of CD16a (FcγRIIIa), the antibody is capable of killing KMS-12BM cells by ADCC with an EC 50 of about 0.6 ng/mL and/or
b) in the presence of Natural Killer cells expressing the lower affinity variant (158F) of CD16a (FcγRIIIa), the antibody is capable of killing KMS-12BM cells by ADCC with an EC 50 of about 0.65 ng/mL and/or
c) in the presence of Natural Killer cells expressing the higher affinity variant (158V) of CD16a (FcγRIIIa), the antibody is capable of killing RPMI-8226 cells by ADCC with an EC 50 of about 0.09 ng/mL and/or
d) in the presence of Natural Killer cells expressing the lower affinity variant (158F) of CD16a (FcγRIIIa), the antibody is capable of killing RPMI-8226 cells by ADCC with an EC 50 of about 0.09 ng/mL and/or
e) in the presence of Natural Killer cells expressing the higher affinity variant (158V) of CD16a (FcγRIIIa), the antibody is capable of killing MOLP-8 cells by ADCC with an EC 50 of about 0.14 ng/mL and/or
f) in the presence of Natural Killer cells expressing the lower affinity variant (158F) of CD16a (FcγRIIIa), the antibody is capable of killing MOLP-8 cells by ADCC with an EC 50 of about 0.28 ng/mL.

12. The pharmaceutical composition of claim 10, wherein in the presence of human PMBCs expressing the higher affinity variant (158V) of CD16a (FcγRIIIa), the antibody is capable of killing MOLP-8 cells by ADCP with an EC 50 of about 31.87 ng/mL.

13. The pharmaceutical composition of claim 2, wherein the antibody is capable of improving survival of mice in a murine tumor model, wherein mice in the model express human CD16a (158F), and wherein the mice have been injected with 500,000 EL4 cells expressing human CD38.

14. A method for preparing a pharmaceutical composition comprising an antibody that specifically binds human CD38, wherein the antibody comprises
a) a heavy chain (HC) having an amino acid sequence of SEQ ID NO: 2 and a light chain (LC) having an amino acid sequence of SEQ ID NO: 7, or
b) a heavy chain (HC) having an amino acid sequence of SEQ ID NO: 3 and a light chain (LC) having an amino acid sequence of SEQ ID NO: 7, or
c) a heavy chain (HC) having an amino acid sequence of SEQ ID NO: 4 and a light chain (LC) having an amino acid sequence of SEQ ID NO: 7, or
d) a heavy chain (HC) having an amino acid sequence of SEQ ID NO: 5 and a light chain (LC) having an amino acid sequence of SEQ ID NO: 8, or
e) a heavy chain (HC) having an amino acid sequence of SEQ ID NO: 5 and a light chain (LC) having an amino acid sequence of SEQ ID NO: 9, or
f) a heavy chain (HC) having an amino acid sequence of SEQ ID NO: 6 and a light chain (LC) having an amino acid sequence of SEQ ID NO: 8, or
g) a heavy chain (HC) having an amino acid sequence of SEQ ID NO: 6 and a light chain (LC) having an amino acid sequence of SEQ ID NO: 9,
the method comprising the steps of:
i) expressing the antibody in a cell culture;
ii) subjecting the antibody to at least one purification step selected from the group consisting of chromatography and ultrafiltration to produce a purified antibody solution; and
iii) adjusting the purified antibody solution to produce a formulated antibody comprising
the purified antibody at a concentration of 50 mg/mL,
sucrose at a concentration of 8% w/v,
L-histidine at a concentration of 10 mM, and
polysorbate 80 at a concentration of 0.05% v/v,
wherein the formulated antibody has a pH of 6.2; and
iv) lyophilizing the formulated antibody, thereby preparing the pharmaceutical composition.

15. A method for preparing a reconstituted formulated antibody, comprising
a) providing a lyophilized antibody formulation comprising sucrose, L-histidine, polysorbate 80, and an antibody that specifically binds human CD38; and
b) reconstituting the lyophilized antibody formulation in a diluent, wherein the reconstituted antibody formulation comprises
the antibody at a concentration of 50 mg/mL,
sucrose at a concentration of 8% w/v,
L-Histidine at a concentration of 10 mM, and
polysorbate 80 at a concentration of 0.05% v/v,
wherein the reconstituted antibody formulation has a pH of 6.2;
wherein the antibody comprises
i) a heavy chain (HC) having an amino acid sequence of SEQ ID NO: 2 and a light chain (LC) having an amino acid sequence of SEQ ID NO: 7, or
ii) a heavy chain (HC) having an amino acid sequence of SEQ ID NO: 3 and a light chain (LC) having an amino acid sequence of SEQ ID NO: 7, or
iii) a heavy chain (HC) having an amino acid sequence of SEQ ID NO: 4 and a light chain (LC) having an amino acid sequence of SEQ ID NO: 7, or
iv) a heavy chain (HC) having an amino acid sequence of SEQ ID NO: 5 and a light chain (LC) having an amino acid sequence of SEQ ID NO: 8, or
v) a heavy chain (HC) having an amino acid sequence of SEQ ID NO: 5 and a light chain (LC) having an amino acid sequence of SEQ ID NO: 9, or
vi) a heavy chain (HC) having an amino acid sequence of SEQ ID NO: 6 and a light chain (LC) having an amino acid sequence of SEQ ID NO: 8, or
vii) a heavy chain (HC) having an amino acid sequence of SEQ ID NO: 6 and a light chain (LC) having an amino acid sequence of SEQ ID NO: 9.

16. A method of treating a patient suffering from a hematological disease, comprising administering to the patient one or more doses of an antibody that specifically binds human CD38, wherein the patient has a disease that comprises CD38-expessing cells, wherein the antibody comprises
a) a heavy chain (HC) having an amino acid sequence of SEQ ID NO: 2 and a light chain (LC) having an amino acid sequence of SEQ ID NO: 7, or
b) a heavy chain (HC) having an amino acid sequence of SEQ ID NO: 3 and a light chain (LC) having an amino acid sequence of SEQ ID NO: 7, or
c) a heavy chain (HC) having an amino acid sequence of SEQ ID NO: 4 and a light chain (LC) having an amino acid sequence of SEQ ID NO: 7, or
d) a heavy chain (HC) having an amino acid sequence of SEQ ID NO: 5 and a light chain (LC) having an amino acid sequence of SEQ ID NO: 8, or
e) a heavy chain (HC) having an amino acid sequence of SEQ ID NO: 5 and a light chain (LC) having an amino acid sequence of SEQ ID NO: 9, or f) a heavy chain (HC) having an amino acid sequence of SEQ ID NO: 6 and a light chain (LC) having an amino acid sequence of SEQ ID NO: 8, or g) a heavy chain (HC) having an amino acid sequence of SEQ ID NO: 6 and a light chain (LC) having an amino acid sequence of SEQ ID NO: 9.

17. The method of claim 16, wherein the disease of hematological origin is selected from the group consisting of: amyloidosis, non-Hodgkin's lymphoma (NHL), Waldenstrom's disease, multiple myeloma (MM), acute lymphocytic leukemia (ALL), and acute myelogenous leukemia (AML).

18. The method of claim 16, wherein the one or more doses of antibody is provided as a lyophilized antibody formulation and wherein prior to administration, the lyophilized antibody formulation is reconstituted forming a reconstituted antibody formulation such that the reconstituted antibody formulation has a pH of 6.2 and comprises the antibody at a concentration of 50 mg/mL in a liquid comprising 10 mM L-histidine, 8% (w/v) sucrose, and 0.05% (v/v) polysorbate 80.

19. The method of claim 16, wherein the antibody is administered at a dose of 20 mg/kg, 10 mg/kg, 5 mg/kg, 3 mg/kg, or 1.5 mg/kg.

20. The method of claim 16, wherein the pharmaceutical composition comprises a formulated antibody, wherein the formulated antibody comprises the antibody present at a concentration of 50 mg/mL, sucrose at a concentration of 8% (w/v), L-histidine at a concentration of 10 mM, and polysorbate 80 (PS80) at a concentration of 0.05% (v/v), wherein the formulated antibody has a pH of 6.2.

21. The method of claim 16, wherein the antibody has an isoelectric point (pI) of 5.8 to 9.0 when measured by capillary isoelectric focusing (cIEF).

22. The method of claim 16, wherein amino acid at position 1 of the HC amino acid sequence is pyroglutamine.

23. The method of claim 16, wherein the antibody comprises a main charge variant and at least one acidic charge variant and wherein the antibody has at least one of
a) the HC of the at least one charge variant comprises at least one deamidated asparagine selected from the group consisting of N289, N318, N387, and N392 as numbered according to SEQ ID NO: 1, or
b) the antibody comprises a main charge variant and least one acidic charge variant, wherein the main charge variant comprises at least 71% of the antibody and the acidic charge variant comprises no more than 30% of the antibody, or
c) the main charge variant has an isoelectric point (pI) of 7.5 and wherein the one or more acidic charge variant has pI of 5.8 when measured by capillary isoelectric focusing (cIEF).

24. The method of claim 16, wherein the antibody comprises at least one basic charge variant, and wherein the antibody has at least one of
a) the basic charge variant comprises no more than 4% of the antibody, or
b) the one or more basic charge variants has a pI of 9.0 when measured by capillary isoelectric focusing (cIEF).

* * * * *

SEQUENCE LISTING

```
<160> NUMBER OF SEQ ID NOS: 14

<210> SEQ ID NO 1
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 1

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
```

```
                    35                  40                  45
Gly Thr Ile Tyr Pro Gly Asp Gly Asp Thr Gly Tyr Ala Gln Lys Phe
 50                  55                  60

Gln Gly Lys Ala Thr Leu Thr Ala Asp Lys Ser Ser Lys Thr Val Tyr
 65                  70                  75                  80

Met His Leu Ser Ser Leu Ala Ser Glu Asp Ser Ala Val Tyr Tyr Cys
                 85                  90                  95

Ala Arg Gly Asp Tyr Tyr Gly Ser Asn Ser Leu Asp Tyr Trp Gly Gln
                100                 105                 110

Gly Thr Ser Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450
```

<210> SEQ ID NO 2
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 2

```
Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
                20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
    355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly

<210> SEQ ID NO 3
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 3

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 4
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 4

```
Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                    180                 185                 190
        Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Ala Gly
        225                 230                 235                 240

Pro Asp Val Phe Leu Phe Pro Pro Lys Pro Lys Asp Thr Leu Met Ile
                        245                 250                 255

Ser Arg Thr Pro Glu Val Thr Cys Val Val Val Asp Val Ser His Glu
                    260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Leu Pro Glu Glu
                        325                 330                 335

Lys Thr Ile Ser Lys Ala Lys Gly Gln Pro Arg Glu Pro Gln Val Tyr
                    340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                435                 440                 445

Gly

<210> SEQ ID NO 5
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 5

Gln Val Gln Leu Val Gln Ser Gly Ala Glu Val Ala Lys Pro Gly Ala
        1               5                   10                  15

Ser Val Lys Val Ser Cys Lys Ala Ser Gly Tyr Thr Phe Thr Asp Tyr
                    20                  25                  30

Trp Met Gln Trp Val Arg Gln Ala Pro Gly Gln Gly Leu Glu Trp Ile
                35                  40                  45

Gly Thr Ile Tyr Pro Gly Asp Gly Asp Thr Ser Tyr Ala Gln Lys Phe
            50                  55                  60

Gln Gly Arg Val Thr Met Thr Ala Asp Thr Ser Thr Ser Thr Val Tyr
        65                  70                  75                  80

Met Glu Leu Ser Ser Leu Arg Ser Glu Asp Thr Ala Val Tyr Tyr Cys
                        85                  90                  95
```

```
Ala Arg Gly Asp Tyr Tyr Gly Ser Asn Ser Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 6
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 6
```

```
Gln Val Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
        50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
```

-continued

```
           420                 425                 430
Glu Ala Leu His Asn His Tyr Thr Gln Lys Ser Leu Ser Leu Ser Pro
            435                 440                 445
Gly

<210> SEQ ID NO 7
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 7

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asp Val Ser Thr Val
            20                  25                  30

Leu Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Ser Gly
```

```
            50                  55                  60
Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln His Tyr Ser Pro Pro Tyr
                 85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

```
<210> SEQ ID NO 9
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 9

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Asp Val Ser Thr Val
                 20                  25                  30

Val Ala Trp Tyr Gln Gln Lys Pro Gly Gln Ser Pro Arg Arg Leu Ile
             35                  40                  45

Tyr Ser Ala Ser Tyr Arg Tyr Ile Gly Val Pro Asp Arg Phe Ser Gly
         50                  55                  60

Ser Gly Ser Gly Thr Asp Phe Thr Phe Thr Ile Ser Ser Leu Gln Ala
 65                  70                  75                  80

Glu Asp Val Ala Val Tyr Tyr Cys Gln Gln His Tyr Ser Pro Pro Tyr
                 85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
                195                 200                 205
Phe Asn Arg Gly Glu Cys
    210

<210> SEQ ID NO 10
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 10

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
```

```
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 11
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 11

Met Trp Gln Leu Leu Pro Thr Ala Leu Leu Leu Val Ser Ala
1               5                   10                  15
Gly Met Arg Thr Glu Asp Leu Pro Lys Ala Val Val Phe Leu Glu Pro
                20                  25                  30
Gln Trp Tyr Arg Val Leu Glu Lys Asp Ser Val Thr Leu Lys Cys Gln
            35                  40                  45
Gly Ala Tyr Ser Pro Glu Asp Asn Ser Thr Gln Trp Phe His Asn Glu
        50                  55                  60
Ser Leu Ile Ser Ser Gln Ala Ser Ser Tyr Phe Ile Asp Ala Ala Thr
65                  70                  75                  80
Val Asp Asp Ser Gly Glu Tyr Arg Cys Gln Thr Asn Leu Ser Thr Leu
                85                  90                  95
Ser Asp Pro Val Gln Leu Glu Val His Ile Gly Trp Leu Leu Leu Gln
                100                 105                 110
Ala Pro Arg Trp Val Phe Lys Glu Glu Asp Pro Ile His Leu Arg Cys
            115                 120                 125
His Ser Trp Lys Asn Thr Ala Leu His Lys Val Thr Tyr Leu Gln Asn
        130                 135                 140
Gly Lys Gly Arg Lys Tyr Phe His His Asn Ser Asp Phe Tyr Ile Pro
145                 150                 155                 160
Lys Ala Thr Leu Lys Asp Ser Gly Ser Tyr Phe Cys Arg Gly Leu Val
                165                 170                 175
Gly Ser Lys Asn Val Ser Ser Glu Thr Val Asn Ile Thr Ile Thr Gln
                180                 185                 190
Gly Leu Ala Val Ser Thr Ile Ser Ser Phe Phe Pro Pro Gly Tyr Gln
            195                 200                 205
Val Ser Phe Cys Leu Val Met Val Leu Leu Phe Ala Val Asp Thr Gly
        210                 215                 220
Leu Tyr Phe Ser Val Lys Thr Asn Ile Arg Ser Ser Thr Arg Asp Trp
225                 230                 235                 240
Lys Asp His Lys Phe Lys Trp Arg Lys Asp Pro Gln Asp Lys
                245                 250
```

<210> SEQ ID NO 12
<211> LENGTH: 317
<212> TYPE: PRT
<213> ORGANISM: Artificial sequence
<220> FEATURE:
<223> OTHER INFORMATION: Synthetic polypeptide

<400> SEQUENCE: 12

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp Ala
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Lys Asn Ile Tyr
    290                 295                 300

Leu Thr Leu Pro Pro Asn Asp His Val Asn Ser Asn Asn
305                 310                 315
```

<210> SEQ ID NO 13
<211> LENGTH: 452
<212> TYPE: PRT
<213> ORGANISM: Artificial sequence
<220> FEATURE:
<223> OTHER INFORMATION: Synthetic polypeptide

<400> SEQUENCE: 13

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 14
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```